(12) United States Patent
Ceccarelli et al.

(10) Patent No.: US 9,139,593 B2
(45) Date of Patent: Sep. 22, 2015

(54) AZETIDINE COMPOUNDS, COMPOSITIONS AND METHODS OF USE

(71) Applicant: Hoffman-La Roche Inc., Nutley, NJ (US)

(72) Inventors: Simona M. Ceccarelli, Basel (CH); Carine Guerot, Herts (GB); Henner Knust, Rheinfelden (DE)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 14/328,033

(22) Filed: Jul. 10, 2014

(65) Prior Publication Data

US 2014/0323462 A1 Oct. 30, 2014

Related U.S. Application Data

(63) Continuation of application No. 13/661,072, filed on Oct. 26, 2012, now Pat. No. 8,809,552.

(30) Foreign Application Priority Data

Nov. 1, 2011 (EP) ..................................... 11187364

(51) Int. Cl.

| | | |
|---|---|---|
| *C07D 229/02* | (2006.01) | |
| *C07D 205/04* | (2006.01) | |
| *C07D 209/52* | (2006.01) | |
| *C07D 239/02* | (2006.01) | |
| *C07D 239/42* | (2006.01) | |
| *A61K 31/397* | (2006.01) | |
| *A61K 31/505* | (2006.01) | |
| *A61K 31/46* | (2006.01) | |
| *C07D 487/10* | (2006.01) | |
| *C07D 487/04* | (2006.01) | |
| *C07D 205/12* | (2006.01) | |

(52) U.S. Cl.
CPC ............ *C07D 487/10* (2013.01); *C07D 205/12* (2013.01); *C07D 487/04* (2013.01)

(58) Field of Classification Search
USPC ...................... 548/210.16, 275, 412; 544/323
See application file for complete search history.

(56) References Cited

U.S. PATENT DOCUMENTS

| | | | | |
|---|---|---|---|---|
| 4,780,468 | A | * 10/1988 | Bridges et al. ................ | 514/312 |
| 2011/0071129 | A1 | * 3/2011 | Ando et al. .............. | 514/210.16 |
| 2015/0065481 | A1 | * 3/2015 | Sulzer-Mosse et al. . | 514/210.18 |

FOREIGN PATENT DOCUMENTS

| | | |
|---|---|---|
| CA | 2025005 | 3/1991 |
| CN | 102093320 | 6/2011 |
| WO | 2008051873 | 5/2008 |
| WO | WO 2010108651 A1 * | 9/2010 |
| WO | 2013065712 | 5/2013 |

OTHER PUBLICATIONS

The English translation of the Japanese Office Action, issued on Jan. 6, 2015, in the corresponding Japanese Application No. 2014-539307.
The English translation of the Chinese Office Action, issued on May 25, 2015, in related Chinese Application No. 201280053329.3.
Burkhard et al., "2,6-Diazaspiro[3.3]heptanes: Synthesis and Application in Pd-Catalyzed Aryl Animation Reactions," Org. Lett., 2008, 10(16), pp. 3525-3526.
Hamza et al., "Synthesis of novel 2,6-Diazaspiro[3.3]heptanes, "Synlett 2007(16): 2584-2586.

* cited by examiner

*Primary Examiner* — Nyeemah A Grazier

(57) ABSTRACT

Provided are compounds of Formula I, $$R^1\text{-}L^1\text{-}A\text{-}L^2\text{-}R^2 \qquad (I),$$

and stereoisomers, tautomers and pharmaceutically acceptable salts thereof, wherein A, $L^1$, $L^2$, $R^1$ and $R^2$ are defined herein. The present invention also provides a pharmaceutical composition and methods of using such compounds. The compounds are useful for therapy and/or prophylaxis in a patient, and in particular to inhibitors of Soluble Epoxide Hydrolase (sEH).

8 Claims, No Drawings

AZETIDINE COMPOUNDS, COMPOSITIONS AND METHODS OF USE

CROSS-REFERENCE TO RELATED APPLICATIONS

This application is a continuation of U.S. application Ser. No. 13/661,072, filed Oct. 26, 2012, now pending, which claims the benefit of European Patent Application No. 11187364.2, filed Nov. 1, 2011, both of which are hereby incorporated herein by reference in their entireties.

FIELD OF THE INVENTION

The present invention relates to azetidine derivatives useful for therapy and/or prophylaxis in a patient, and in particular to inhibitors of Soluble Epoxide Hydrolase (sEH). The compounds are useful for treating disease states mediated by sEH, including genitourinary disease states, pain diseases states, respiratory disease states, cardiovascular disease states, metabolic disease states, neurological disease states, immunological disease states, inflammatory disease states, cancer, nephropathy, stroke, endothelial dysfunction, prevention of ischemic events and end organ protection.

BACKGROUND OF THE INVENTION

Epoxide hydrolases are a group of enzymes that catalyze the addition of water to an epoxide, resulting in a vicinal diol (Hammock et al (1997) in *Comprehensive Toxicology: Biotransformation* (Elsevier, New York), pp. 283-305). Several types of epoxide hydrolases have been characterized in mammals including soluble epoxide hydrolase (sEH), also known as cytosolic epoxide hydrolase, cholesterol epoxide hydrolase, leukotriene A4 (LTA$_4$) hydrolase, hepoxilin epoxide hydrolase and microsomal epoxide hydrolase (mEH) (Fretland and Omiecinski, *Chemico-Biological Interactions*, 129: 41-59 (2000)). Epoxide hydrolases have been found in a variety of tissues in vertebrates including heart, kidney and liver.

sEH in humans (hsEH, EPHX2) is a bifunctional homodimeric enzyme located in both cytosol and peroxisomes with hydrolase and phosphatase activity (Newman et al, *Prog. Lipid Res*, 44: 1-51(2005)). Specifically the C terminus hydrolase motif of sEH transforms four regioisomers of epoxyeicosatrienoic acids (EETs), namely 5,6-, 8,9-, 11,12-, and 14,15-epoxyeicosatrienoic acids (EETs). The products generated by hydrolysis of these substrates are the dihydroxyeicosatrienoic acids or DHETS, 5,6-, 8,9-, 11,12-, and 14,15-dihydroxyeicosatrienoic acid respectively, whereby the biological effects of EETs are diminished or eliminated (Yu et al., *Circ. Res*, 87: 992-7 (2000)). Also known to be substrates are epoxides of linoleic acid known as leukotoxin or isoleukotoxin. Both the EETs and the leukotoxins are generated by members of the cytochrome P450 monooxygenase family (Capdevila et al., *J. Lipid Res.*, 41: 163-181 (2000)).

The structural requirements for substrates of sEH have recently been described (Morisseau et al., *Biochem. Pharmacol.* 63:1599-1608 (2002)) and the crystal structure, as well as structures of co-crystals with inhibitors determined (Argiriadi et al., *Proc. Natl. Acad. Sci. USA* 96: 10637-10642 (1999)). A variety of inhibitors of sEH have also been described (Mullin and Hammock, *Arch. Biochem. Biophys.* 216:423-439 (1982), Morisseau et al., *Proc. Natl. Acad. Sci. USA* 96:8849-8854 (1999), McElroy et al., *J. Med. Chem.* 46:1066-1080 (2003)). A phosphatase activity for phosphorylated forms of hydroxy unsaturated fatty acids has recently been described for soluble epoxide hydrolase, making this a bifunctional enzyme (Newman et al., *Proc. Natl. Acad. Sci. USA* 100:1558-1563 (2003)).

The physiological role of EETs has best been established in vasodilation of vascular beds. Evidence has accumulated that EETs in fact function as endothelium-derived hyperpolarizing factors or EDHFs (Campbell et al., *Circ. Res.* 78:415-423 (1996)). EETs are formed in endothelial cells, induce vasodilation in vascular smooth muscle cells by a mechanism that results in activation of "maxi K" potassium channels with attendant hyperpolarization and relaxation (Hu and Kim, *Eur. J. Pharmacol.* 230:215-221 (1993)). It has been shown that 14,15-EET exerts its physiological effects by binding to cell surface receptors that are regulated by intracellular cyclic AMP and by a signal transduction mechanism involving protein kinase A (Wong et al., *J. Lipid Med. Cell Signal.* 16:155-169 (1997)). More recently, this EET dependent relaxation in coronary smooth muscle was demonstrated to occur through a guanine nucleotide binding protein, $G_s\alpha$, accompanied by ADP-ribosylation (Li et al., *Circ. Res.* 85:349-56 (1999)). Alternatively, the cation channel TRPV4, has recently been shown to be activated by 5,6-EET in mouse aorta vascular endothelial cells (Watanabe et al., *Nature* 424:434-438 (2003)). This has generated interest in EETs and soluble epoxide hydrolase as targets for antihypertensives. Indeed, male sEH knockout mice have reduced blood pressure as compared to wild type controls (Sinal et al., *J. Biol. Chem.* 275:40504-40510 (2000)). Furthermore, inhibition of sEH in spontaneously hypertensive rats caused a reduction in blood pressure (Yu et al., *Circ. Res.* 87:992-998 (2000)).

EET mimics or pharmacological interventions to either increase the synthesis of EETs or prevent degradation of EETs (with reduced levels of DHETs) have been proposed as a potential therapeutic strategy for a variety of diseases. It has been further postulated that inhibition of the NF-kappaB pathway resulting from sEH inhibition could have therapeutic effects with regard to a variety of disease states (Shen, *Expert Opin. Ther. Patents*, 20(7): 941-956 (2010)).

sEH inhibitors were demonstrated as useful for the treatment of inflammatory disease states, e.g. rheumatoid arthritis, and cardiovascular disease states, such as hypertension, myocardial infarction, renal diseases and ischemic stroke (Fang et al, *Drugs of the Future*, 34(7): 579-585 (2009), Shen, *Expert Opin. Ther. Patents*, 20(7): 941-956 (2010), US20070117782; WO2003/002555).

A further indication of sEH inhibitors was claimed to be nephropathy in patients with type II diabetes (US20090018092 and WO2005/089380).

Inhibitors of sEH can be useful for the treatment of genitourinary disease states, including smooth muscle disorder states such as erectile dysfunction, overactive bladder, uterine contractions and irritable bowel syndrome (US20090270452, US2009082402, WO2008/074678).

sEH inhibitors were proposed to reduce pulmonary infiltration by neutrophils (US20050222252, WO2005/094373) and appeared to be synergistic in reducing the number of neutrophils in lung indicating that sEH inhibitors may be useful to treat obstructive pulmonary disease states, restrictive airway disease states and asthma (Shen, *Expert Opin. Ther. Patents*, 20(7): 941-956 (2010), US20050222252).

sEH inhibitors were also claimed to be useful for the treatment of neuropathic pain (WO2009/062073).

sEH inhibitors were further reported to be useful for the treatment of metabolic syndromes, including obesity, hypertension, diabetes and hypercholesterolemia (Shen, *Expert Opin. Ther. Patents*, 20(7): 941-956 (2010), US20080221105).

It appeared that sEH inhibitors are effective in the treatment of T-lymphocyte mediated immunological and autoimmunological disease states (WO2000/23060).

Further studies revealed the effect of sEH inhibitors on the reduction of damage from stroke (US20060148744).

Objects of the present invention are new compounds of Formula I, stereoisomers, tautomers or pharmaceutically acceptable salts thereof, their use for the treatment of disease states mediated by sEH, including genitourinary disease states, pain disease states, respiratory disease states, cardiovascular disease states, metabolic disease states, neurological disease states, immunological disease states, inflammatory disease states, cancer, nephropathy, stroke, endothelial dysfunction, prevention of ischemic events and end organ protection, and medicaments based on a compound in accordance with the invention in the control or prevention of illnesses.

SUMMARY OF THE INVENTION

The invention relates to azetidine derivatives of Formula I:

(I)

wherein
A is selected from the group consisting of Ia, Ib or Ic:

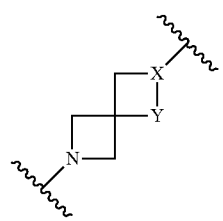
Ia wherein
X is N or CH;
Y is NH or $CH_2$; or

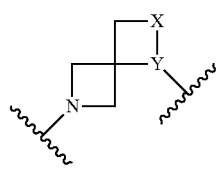
Ib wherein
X is NH or $CH_2$;
Y is N or CH; or

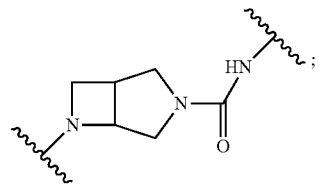
Ic wherein
$L^1$ is selected from the group consisting of a bond, $—(CH_2)_{1-3}—$, $—NH—(CH_2)_{0-3}—C(O)—$, $—(CH_2)_{0-3}—C(O)—$, $—(CH_2)_{0-3}—SO_2—$ and $—(CH_2)_{0-3}—NR^3—C(O)—$;

$L^2$ is selected from the group consisting of a bond, $—(CH_2)_{1-3}—$, $—C(O)—(CH_2)_{0-3}—NH—$, $—NH—(CH_2)_{0-3}—C(O)—NH—$, $—(CH_2)_{0-3}—C(O)—$, $—(CH_2)_{0-3}—SO_2—$ and $—(CH_2)_{0-3}—NR^3—C(O)—$;

$R^1$ is selected from the group consisting of phenyl, 5- or 6-membered heteroaryl, adamantyl and $—(CH_2)_{1-3}$-phenyl, wherein said phenyl, heteroaryl or adamantyl is unsubstituted or substituted by one to three $R^5$ groups;

$R^2$ is selected from the group consisting of phenyl, 5- or 6-membered heteroaryl and $—(CH_2)_{1-3}$-phenyl, wherein said phenyl or heteroaryl is unsubstituted or substituted by one to three $R^5$ groups;

$R^3$ is hydrogen or lower alkyl;
$R^4$ is hydrogen or lower alkyl; and
$R^5$ is selected from the group consisting of halogen, lower alkyl, lower haloalkyl, lower haloalkoxy, and $—C(O)OR^4$, or a stereoisomer, tautomer or pharmaceutically acceptable salt thereof, with the proviso that said compound is not (4-bromophenyl)[6-[(4-methylphenyl)sulfonyl]-1,6-diazaspiro[3,3]hept-1-yl]methanone, 6-[(4-methylphenyl)sulfonyl]-1-(phenylmethyl)-1,6-diazaspiro[3,3]heptane, 2,6-bis[(4-methylphenyl)sulfonyl]-2,6-diazaspiro[3,3]heptane and 2-phenyl-6-(phenylmethyl)-2,6-diazaspiro[3,3]heptane, and the further provisos that when $L^2$ is $—C(O)—NH—$, $L^1$ is not $—CH_2—$; when $L^2$ is $—CH_2—$, $L^1$ is not a bond; when $L^2$ is $—SO_2—$, $L^1$ is not $—CH_2—$; and $L^1$ and $L^2$ are different.

DETAILED DESCRIPTION OF THE INVENTION

Definitions

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10th Ed., McGraw Hill Companies Inc., New York (2001).

The phrase "a" or "an" entity as used herein refers to one or more of that entity; for example, a compound refers to one or more compounds or at least one compound. As such, the terms "a" (or "an"), "one or more", and "at least one" can be used interchangeably herein.

As used in this specification, whether in a transitional phrase or in the body of the claim, the terms "comprise(s)" and "comprising" are to be interpreted as having an open-ended meaning That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

As used herein, unless specifically indicated otherwise, the terms "including" and "include(s) are used in the "including, but not limited" sense.

The term "alkyl" refers to a saturated linear or branched-chain monovalent hydrocarbon radical having one to seven C-atoms ($C_1$-$C_7$ alkyl). In particular, alkyl is "lower alkyl", i.e. ($C_1$-$C_6$) alkyl. $C_0$ refers to a bond. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$) and 1-heptyl.

The terms "haloalkyl" or "lower haloalkyl" refers to "alkyl" or "lower alkyl" as defined herein, wherein one or more carbon atoms are substituted with one or more halogen atoms.

The term "alkoxy" as used herein means an —O-alkyl group, wherein "alkyl" is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an "alkoxy" group with a "lower alkyl" group as previously defined.

The terms "haloalkoxy" or "lower haloalkoxy" refer to an "alkoxy" or "lower alkoxy" group, wherein one or more carbon atoms are substituted with one or more halogen atoms.

"Halo" or "halogen" refer to F, Cl, Br or I.

The term "heteroaryl" refers to 5- or 6-membered aromatic carbocyclic radicals in which at least one ring atom is a nitrogen, the remaining ring atoms being carbon. Examples for "heteroaryl" include pyrrolyl, pyrazolyl, imidazolyl, pyridinyl, pyrimidinyl, pyridazinyl and pyrazinyl. In particular, "heteroaryl" is pyrimidinyl.

The term "genitourinary disease state" refers to disease states associated with the urinary tract, including overactive bladder; outlet obstruction; outlet insufficiency; benign prostatic hyperplasia; interstitial cystitis; male erectile dysfunction and pelvic hypersensitivity. In particular, the compounds of the present invention may be useful in the treatment of symptoms associated with the above disease state, e.g., urgency, frequency, altered bladder capacity, incontinence, micturition threshold, unstable bladder contractions, sphincteric spasticity, detrusor hyperreflexia (neurogenic bladder), detrusor instability, benign prostatic hyperplasia (BPH), urethral stricture disease, tumors, low flow rates, difficulty in initiating urination, urgency, urethral hypermobility, intrinsic sphincteric deficiency, mixed incontinence, stress incontinence, pelvic pain, interstitial (cell) cystitis, prostadynia, prostatis, vulvadynia, urethritis, orchidalgia, and other symptoms related to overactive bladder.

The term "disease state" refers to any disease, condition, symptom, disorder, or indication.

"Respiratory disease state" refers to all disease states of the respiratory tract, including acute bronchitis; asthma; chronic bronchitis; influenza; pulmonary fibrosis; sudden infant death syndrome; adult respiratory distress syndrome; interstitial lung disease; and chronic obstructive pulmonary disease (COPD).

"Pain disease states" means any pain disease state, including neuropathic pain; inflammatory pain; surgical pain; visceral pain; dental pain; premenstrual pain; central pain; chronic pain, pain due to burns; pain due to migraine or cluster headaches; pain due to nerve injury; pain due to neuritis; neuralgias; pain due to poisoning; pain due to ischemic injury; cancer pain; pain related to viral, parasitic or bacterial infection; post-traumatic injury; or pain associated with irritable bowel syndrome.

"Metabolic disease states" means any metabolic disease state, including obesity; hypertension; diabetes; and dyslipidemias, including hypercholesterolemia.

"Inflammatory disease states" mean any disease states characterized by inflammation, including renal inflammation; hepatic inflammation; vascular inflammation; lung inflammation; inflammatory diseases related to the eyes; rheumatoid arthritis (RA); inflammatory bowel disease; Crohn's disease; ulcerative colitis; psoriasis; contact dermatitis; delayed hypersensitivity reactions; ulcerative colitis; allergic rhinitis; or atopic dermatitis. In particular, the inflammatory disease state is rheumatoid arthritis (RA).

"Cardiovascular disease states" means the class of disease states that involve the heart or blood vessels, including cardiac hypertrophy; cardiac arrhythmia; cardiomyopathy; coronary heart disease; atherosclerosis; restenosis; cardiomegaly; myocardial infarction; or congestive heart failure.

"Neurological disease states" means any disease state of the nerve system, including Alzheimer's disease; Pick's disease; corticobasal degeneration; progressive supranuclear palsy; frontotemporal dementia and parkinsonism; amyotrophic lateral sclerosis; Guillain-Barré syndrome; Mobius syndrome; and Tourette syndrome.

"Stroke" means ischemic and hemorrhagic stroke, in particular ischemic stroke.

"End organ protection" refers to protection of major organs fed by the circulatory system from damage due to uncontrolled hypertension, hypotension or hypovolemia, including renal protection, brain protection and cardiac protection.

"Ischemic events" mean the events relating to the ischemic cascade, including reperfusion injuries.

"Immunological disease states" include (1) autoimmune disease states, (2) disease states associated with T-lymphocyte mediated immune responses, (3) transplantation; allograft and xenograft rejection and (4) graft versus host disease.

"Autoimmune disease states" mean any disease states arising from an overactive immune response of the body against substances and tissues normally present in the body, including the following disease states: Hashimoto thyroiditis; systemic lupus erythematous; receptor autoimmunity; autoimmune hemolytic anemia; autoimmune thrombocyogpenic purpura; autoimmune hepatitis; scleroderma; polymyositis; pernicious anemia; idiopathic Addison's disease; adrenergic drug resistance; uticaria and atopic dermatitis; autoimmune angioedema; autoimmune aplastic anemia; autoimmune dysautonomia; autoimmune hepatitis; autoimmune hyperlipidemia; autoimmune immunodeficiency; autoimmune inner ear disease (AIED); autoimmune myocarditis; autoimmune pancreatitis; autoimmune retinopathy; autoimmune thrombocytopenic purpura (ATP); and autoimmune urticarial.

"Disease states associated with T-lymphocyte mediated immune responses" mean any disease states associated with T-lymphocyte mediated immune responses, including the following disease states: multiple sclerosis; psoriasis; erythemas; keratitis; Crohn's disease; rhinitis; eczema; photoallergic sensitivity; endotoxin-shock; and sarcoidosis.

The terms "cancer" and "cancerous" refer to or describe the physiological condition in patients that is typically characterized by unregulated cell growth. A "tumor" comprises one or more cancerous cells. Examples of cancer include carcinoma; lymphoma; blastoma; sarcoma; and leukemia or lymphoid malignancies. More particular examples of such cancers include squamous cell cancer (e.g., epithelial squamous cell cancer); lung cancer, including small-cell lung cancer, non-small cell lung cancer ("NSCLC"), adenocarcinoma of the lung and squamous carcinoma of the lung; cancer of the peritoneum; hepatocellular cancer; gastric or stomach cancer; pancreatic cancer; glioblastoma; cervical cancer; ovarian cancer; liver cancer; bladder cancer; hepatoma; breast cancer; colon cancer; rectal cancer; colorectal cancer; endometrial or uterine carcinoma; salivary gland carcinoma; kidney or renal cancer; prostate cancer; vulvar cancer; thyroid cancer; hepatic carcinoma; anal carcinoma; penile carcinoma; as well as head and neck cancer.

The phrase "therapeutically effective amount" means an amount of a compound of the present invention that (i) treats or prevents the particular disease state, (ii) attenuates, ameliorates or eliminates one or more symptoms of the particular disease state, or (iii) prevents or delays the onset of one or more symptoms of the particular disease state described herein. In the case of cancer, the therapeutically effective amount of the drug may reduce the number of cancer cells; reduce the tumor size; inhibit (i.e., slow to some extent and alternatively stop) cancer cell infiltration into peripheral organs; inhibit (i.e., slow to some extent and alternatively stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR). In the case of immunological disease states, the therapeutic effective amount is an amount sufficient to decrease or alleviate an allergic disorder, the symptoms of an autoimmune and/or inflammatory disease state, or the symptoms of an acute inflammatory reaction (e.g. asthma).

The term "stereoisomers" refers to compounds which have identical chemical constitution, but differ with regard to the arrangement of the atoms or groups in space. Stereoisomers include diastereomers, enantiomers and the like.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt," as used herein, refers to pharmaceutically acceptable organic or inorganic salts of a compound comprised by this application. "Pharmaceutically acceptable salts" include both acid and base addition salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion, for example a dihydrochloride or diformate salt.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, tromethamine, dicyclohexylamine, choline, and caffeine.

sEH Inhibitor Compounds

The invention relates to azetidine derivatives of Formula I:

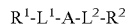

(I)

wherein
A is selected from the group consisting of Ia, Ib or Ic:

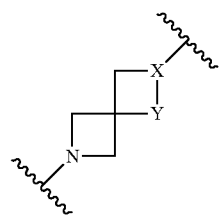

Ia wherein
X is N or CH;
Y is NH or $CH_2$; or

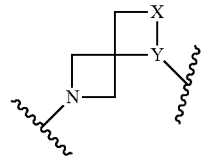

Ib wherein
X is NH or $CH_2$;
Y is N or CH; or

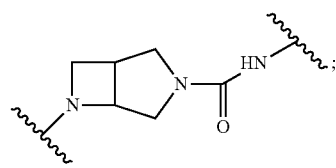

Ic wherein
$L^1$ is selected from the group consisting of a bond, —$(CH_2)_{1-3}$—, —NH—$(CH_2)_{0-3}$—C(O)—, —$(CH_2)_{0-3}$—C(O)—, —$(CH_2)_{0-3}$—$SO_2$— and —$(CH_2)_{0-3}$—$NR^3$—C(O)—;
$L^2$ is selected from the group consisting of a bond, —$(CH_2)_{1-3}$—, —C(O)—$(CH_2)_{0-3}$—NH—, —NH—$(CH_2)_{0-3}$—C(O)—NH—, —$(CH_2)_{0-3}$—C(O)—NH—, —$(CH_2)_{0-3}$—C(O)—, —$(CH_2)_{0-3}$—$SO_2$— and —$(CH_2)_{0-3}$—$NR^3$—C(O)—;
$R^1$ is selected from the group consisting of phenyl, 5- or 6-membered heteroaryl, adamantyl and —$(CH_2)_{1-3}$-phenyl, wherein said phenyl, heteroaryl or adamantyl is unsubstituted or substituted by one to three $R^5$ groups;
$R^2$ is selected from the group consisting of phenyl, 5- or 6-membered heteroaryl and —$(CH_2)_{1-3}$-phenyl, wherein said phenyl or heteroaryl is unsubstituted or substituted by one to three $R^5$ groups;
$R^3$ is hydrogen or lower alkyl;
$R^4$ is hydrogen or lower alkyl; and
$R^5$ is selected from the group consisting of halogen, lower alkyl, lower haloalkyl, lower haloalkoxy, and —C(O)$OR^4$, or a stereoisomer, tautomer or pharmaceutically acceptable salt thereof,
with the proviso that said compound is not (4-bromophenyl)[6-[(4-methylphenyl)sulfonyl]-1,6-diazaspiro[3.3]hept-1-yl]methanone, 6-[(4-methylphenyl)sulfonyl]-1-(phenylmethyl)-1,6-diazaspiro[3.3]heptane, 2,6-bis[(4-methylphenyl)sulfonyl]-2,6-diazaspiro[3.3]heptane and 2-phenyl-6-(phenylmethyl)-2,6-diazaspiro[3.3]heptane,
and the further provisos that when $L^2$ is —C(O)—NH—, $L^1$ is not —$CH_2$—; when $L^2$ is —$CH_2$—, $L^1$ is not a bond; when $L^2$ is —$SO_2$—, $L^1$ is not —$CH_2$—; and $L^1$ and $L^2$ are different.

The compounds of this application which include at least one —C(=O)—NH— group exhibit unexpectedly enhanced inhibitory activity compared to analogues with other side chains.

Unless specified otherwise, the wavy line indicates the place of attachment.

In one embodiment, the compound is a compound of Formula I, wherein X is N and Y is $CH_2$:

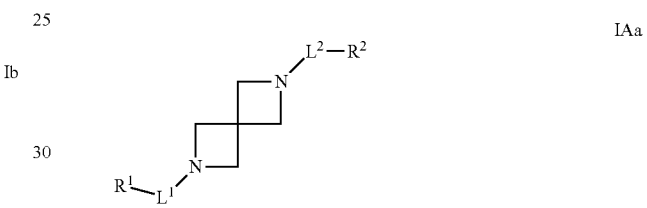

IAa wherein
$L^1$ is selected from the group consisting of a bond, —$(CH_2)_{0-3}$—C(O)—, and —$(CH_2)_{0-3}$—$SO_2$—;
$L^2$ is —C(O)—$(CH_2)_{0-3}$—NH—;
$R^1$ is phenyl or 5- or 6-membered heteroaryl, wherein said phenyl or heteroaryl is unsubstituted or substituted by one $R^5$ group;
$R^2$ is phenyl or —$(CH_2)_{1-3}$-phenyl, wherein said phenyl is unsubstituted or substituted by two $R^5$ groups;
$R^4$ is hydrogen; and
$R^5$ is —C(O)$OR^4$, or a stereoisomer, tautomer or pharmaceutically acceptable salt thereof.

In one embodiment, the compound is a compound of Formula IAa, wherein $L^1$ is selected from the group consisting of a bond, —C(O)— and —$SO_2$—.

In one embodiment, the compound is a compound of Formula IAa, wherein $L^1$ is selected from the group consisting of a bond, —C(O)— and —$SO_2$— and $R^1$ is phenyl or pyrimidinyl, wherein said phenyl or pyrimidinyl is unsubstituted or substituted by one $R^5$ group.

In one embodiment, the compound is a compound of Formula IAa, wherein $L^1$ is selected from the group consisting of a bond, —C(O)— and —$SO_2$— and $R^1$ is phenyl or pyrimidinyl, wherein said phenyl or pyrimidinyl is unsubstituted or substituted by one $R^5$ group in the 4-position.

In one embodiment, the compound is a compound of Formula IAa, wherein $L^1$ is selected from the group consisting of a bond, —C(O)— and —$SO_2$—, and $R^1$ is phenyl or pyrimidinyl wherein said phenyl or pyrimidinyl is unsubstituted or substituted by one $R^5$ group in the 4-position wherein $R^5$ is —C(O)$OR^4$.

In one embodiment, the compound is a compound of Formula IAa, wherein $L^1$ is selected from the group consisting of a bond, —C(O)— and —SO$_2$—, and R$^1$ is phenyl or pyrimidinyl wherein said phenyl or pyrimidinyl is unsubstituted or substituted by one R$^5$ group in the 4-position wherein R$^5$ is —C(O)OH.

In one embodiment, the compound is a compound of Formula IAa, wherein L$^1$ is selected from the group consisting of a bond, —C(O)— and —SO$_2$—, R$^1$ is phenyl or pyrimidinyl wherein said phenyl or pyrimidinyl is unsubstituted or substituted by one R$^5$ group in the 4-position wherein R$^5$ is —C(O)OH, and L$^2$ is —C(O)—NH—.

In one embodiment, the compound is a compound of Formula IAa, wherein L$^1$ is selected from the group consisting of a bond, —C(O)— and —SO$_2$—, R$^1$ is phenyl or pyrimidinyl wherein said phenyl or pyrimidinyl is unsubstituted or substituted by one R$^5$ group in the 4-position wherein R$^5$ is —C(O)OH, L$^2$ is —C(O)—NH— and R$^2$ is —CH$_2$-phenyl unsubstituted or substituted by two R$^5$ groups.

In one embodiment, the compound is a compound of Formula IAa, wherein L$^1$ is selected from the group consisting of a bond, —C(O)— and —SO$_2$—, -, R$^1$ is phenyl or pyrimidinyl wherein said phenyl or pyrimidinyl is unsubstituted or substituted by one R$^5$ group in the 4-position wherein R$^5$ is —C(O)OH, L$^2$ is —C(O)—NH—, and R$^2$ is —CH$_2$-phenyl unsubstituted or substituted by two R$^5$ groups in the 2- and 4-positions.

In one embodiment, the compound is a compound of Formula IAa, wherein L' is selected from the group consisting of a bond, —C(O)— and —SO$_2$—, R$^1$ is phenyl or pyrimidinyl wherein said phenyl or pyrimidinyl is unsubstituted or substituted by one R$^5$ group in the 4-position wherein R$^5$ is —C(O)OH, L$^2$ is —C(O)—NH— and R$^2$ is —CH$_2$-phenyl unsubstituted or substituted by two halogens in the 2- and 4-positions.

In one embodiment, the compound is a compound of Formula IAa, wherein L' is selected from the group consisting of a bond, —C(O)— and —SO$_2$—, R$^1$ is phenyl or pyrimidinyl wherein said phenyl or pyrimidinyl is unsubstituted or substituted by one R$^5$ group in the 4-position wherein R$^5$ is —C(O)OH, L$^2$ is —C(O)—NH—, and R$^2$ is —CH$_2$-phenyl unsubstituted or substituted by two —Cl in the 2- and 4-positions.

In one embodiment the compound is a compound of Formula I, wherein X is CH$_2$ and Y is N:

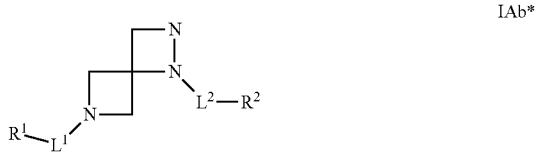

IAb* wherein
L$^1$ is —NH—(CH$_2$)$_{0-3}$—C(O)— or —(CH$_2$)$_{0-3}$—SO$_2$—;
L$^2$ is a selected from the group consisting of bond, —(CH$_2$)$_{1-3}$—, —C(O)—(CH$_2$)$_{0-3}$—NH— and —(CH$_2$)$_{0-3}$—SO$_2$—;
R$^1$ is selected from the group consisting of phenyl, adamantyl and —(CH$_2$)$_{1-3}$-phenyl, wherein said phenyl or adamantyl is unsubstituted or substituted by one or two R$^5$ groups;
R$^2$ is phenyl or —(CH$_2$)$_{1-3}$-phenyl, wherein said phenyl is unsubstituted or substituted by one or two R$^5$ groups; and
R$^5$ is selected from the group consisting of halogen, lower haloalkyl and lower haloalkoxy; or a stereoisomer, tautomer or pharmaceutically acceptable salt thereof.

In one embodiment, the compound is a compound of Formula IAb* wherein L$^1$ is —NH—C(O)— or —SO$_2$—.

In one embodiment, the compound is a compound of Formula IAb* wherein L$^1$ is —NH—C(O)— or —SO$_2$— and R$^1$ is selected from the group consisting of phenyl, adamantyl, —CH$_2$-phenyl, —(CH$_2$)$_2$-phenyl and —(CH$_2$)$_3$-phenyl wherein said phenyl or adamantyl is unsubstituted or substituted by one or two R$^5$ groups.

In one embodiment, the compound is a compound of Formula IAb* wherein L$^1$ is —NH—C(O)— or —SO$_2$— and R$^1$ is selected from the group consisting of phenyl, adamantyl, —CH$_2$-phenyl, —(CH$_2$)$_2$-phenyl and —(CH$_2$)$_3$-phenyl wherein said phenyl or adamantyl is unsubstituted or substituted by one or two R$^5$ groups in the 2- and/or 4-positions.

In one embodiment, the compound is a compound of Formula IAb* wherein L$^1$ is —NH—C(O)— or —SO$_2$— and R$^1$ is selected from the group consisting of phenyl, adamantyl, —CH$_2$-phenyl, —(CH$_2$)$_2$-phenyl and —(CH$_2$)$_3$-phenyl wherein said phenyl or adamantyl is unsubstituted or substituted by one or two R$^5$ groups in 2- and/or 4-positions, wherein said R$^5$ is halogen or lower haloalkoxy.

In one embodiment, the compound is a compound of Formula IAb* wherein L$^1$ is —NH—C(O)— or —SO$_2$— and R$^1$ is selected from the group consisting of phenyl, adamantyl, —CH$_2$-phenyl, —(CH$_2$)$_2$-phenyl and —(CH$_2$)$_3$-phenyl wherein said phenyl or adamantyl is unsubstituted or substituted by one or two R$^5$ groups in the 2- and/or 4-positions, wherein said R$^5$ is —Cl or —OCF$_3$.

In one embodiment, the compound is a compound of Formula IAb* wherein L$^1$ is —NH—C(O)— or —SO$_2$—, R$^1$ is selected from the group consisting of phenyl, adamantyl, —CH$_2$-phenyl, —(CH$_2$)$_2$-phenyl and —(CH$_2$)$_3$-phenyl wherein said phenyl or adamantyl is unsubstituted or substituted by one or two R$^5$ groups, wherein said R$^5$ is —Cl or —OCF$_3$ and L$^2$ is selected from the group consisting of a bond, —CH$_2$—,
—C(O)—NH— and —SO$_2$—.

In one embodiment, the compound is a compound of Formula IAb* wherein L$^1$ is —NH—C(O)— or —SO$_2$—, R$^1$ is selected from the group consisting of phenyl, adamantyl, —CH$_2$-phenyl, —(CH$_2$)$_2$-phenyl and —(CH$_2$)$_3$-phenyl wherein said phenyl or adamantyl is unsubstituted or substituted by one or two R$^5$ groups, wherein said R$^5$ is —Cl or —OCF$_3$, L$^2$ is selected from the group consisting of a bond, —CH$_2$—, —C(O)—NH— and —SO$_2$— and R$^2$ is selected from the group consisting of phenyl, pyrimidinyl and —CH$_2$-phenyl, wherein said phenyl or pyrimidinyl is unsubstituted or substituted by one or two R$^5$ groups.

In one embodiment, the compound is a compound of Formula IAb* wherein L$^1$ is —NH—C(O)— or —SO$_2$—, R$^1$ is selected from the group consisting of phenyl, adamantyl, —CH$_2$-phenyl, —(CH$_2$)$_2$-phenyl and —(CH$_2$)$_3$-phenyl wherein said phenyl or adamantyl is unsubstituted or substituted by one or two R$^5$ groups, wherein said R$^5$ is —Cl or —OCF$_3$, L$^2$ is selected from the group consisting of a bond, —CH$_2$—, —C(O)—NH— and —SO$_2$— and R$^2$ is selected from the group consisting of phenyl, pyrimidinyl and —CH$_2$-phenyl, wherein said phenyl or pyrimidinyl is unsubstituted or substituted by one or two R$^5$ groups in the 2- and/or 4-positions.

In one embodiment, the compound is a compound of Formula IAb* wherein L$^1$ is —NH—C(O)— or —SO$_2$—, R$^1$ is selected from the group consisting of phenyl, adamantyl, —CH$_2$-phenyl, —(CH$_2$)$_2$-phenyl and —(CH$_2$)$_3$-phenyl wherein said phenyl or adamantyl is unsubstituted or substituted by one or two R$^5$ groups, wherein said R$^5$ is —Cl or —OCF$_3$, L$^2$ is selected from the group consisting of a bond, —CH$_2$—, —C(O)—NH— and —SO$_2$— and R$^2$ is selected from the group consisting of phenyl, pyrimidinyl and —CH$_2$-phenyl, wherein said phenyl or pyrimidinyl is unsubstituted or substituted by one or two R$^5$ groups in the 2- and/or 4-positions, wherein said R$^5$ is halogen or lower haloalkyl.

In one embodiment of Formula IAb*, L$^1$ is —NH—C(O)— or —SO$_2$—, R$^1$ is selected from the group consisting of phenyl, adamantyl, —CH$_2$-phenyl, —(CH$_2$)$_2$-phenyl and —(CH$_2$)$_3$-phenyl wherein said phenyl or adamantyl is unsubstituted or substituted by one or two R$^5$ groups, wherein said R$^5$ is —Cl or —OCF$_3$, L$^2$ is selected from the group consisting of a bond, —CH$_2$—, —C(O)—NH— and —SO$_2$— and R$^2$ is selected from the group consisting of phenyl, pyrimidinyl and —CH$_2$-phenyl, wherein said phenyl or pyrimidinyl is unsubstituted or substituted by one or two R$^5$ groups in the 2- and/or 4-positions, wherein said R$^5$ is selected from the group consisting of —F, —Cl and —CF$_3$.

In one embodiment the compound is a compound of Formula I, wherein X is CH$_2$ and Y is CH:

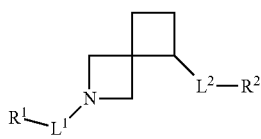

IAb** wherein
L$^1$ is a —(CH$_2$)$_{0-3}$—SO$_2$—;
L$^2$ is —C(O)—(CH$_2$)$_{0-3}$—NH— or —NH—(CH$_2$)$_{0-3}$—C(O)—NH—;
R$^1$ is phenyl, wherein said phenyl is unsubstituted or substituted by one R$^5$ group;
R$^2$ is —(CH$_2$)$_{1-3}$-phenyl, wherein said phenyl is unsubstituted or substituted by two R$^5$ groups; and
R$^5$ is halogen, or a
stereoisomer, tautomer or pharmaceutically acceptable salt thereof In one embodiment, the compound is a compound of Formula IAb** wherein L$^1$ is —SO$_2$—.

In one embodiment, the compound is a compound of Formula IAb** wherein L$^1$ is —SO$_2$— and R$^1$ is phenyl, wherein said phenyl is substituted by one R$^5$ group.

In one embodiment, the compound is a compound of Formula IAb** wherein L$^1$ is —SO$_2$— and R$^1$ is phenyl, wherein said phenyl is substituted by one R$^5$ group in the 2- or 4-position.

In one embodiment, the compound is a compound of Formula IAb** wherein L$^1$ is —SO$_2$— and R$^1$ is phenyl, wherein said phenyl is substituted by one R$^5$ group in the 2- or 4-positions, wherein said R$^5$ is halogen.

In one embodiment, the compound is a compound of Formula IAb** wherein L$^1$ is —SO$_2$— and R$^1$ is phenyl, wherein said phenyl is substituted by one R$^5$ group in the 2- or 4-positions, wherein said R$^5$ is —Cl.

In one embodiment, the compound is a compound of Formula IAb** wherein L$^1$ is —SO$_2$—, R$^1$ is phenyl wherein said phenyl is substituted by one R$^5$ group in the 2- or 4-position, wherein said R$^5$ is —Cl and L$^2$ is —NH—C(O)—NH— or —C(O)—NH—.

In one embodiment, the compound is a compound of Formula IAb** wherein L$^1$ is —SO$_2$—, R$^1$ is phenyl wherein said phenyl is substituted by one R$^5$ group in the 2- or 4-position, wherein said R$^5$ is —Cl, L$^2$ is —NH—C(O)—NH— or —C(O)—NH— and R$^2$ is selected from the group consisting of —CH$_2$-phenyl, —(CH$_2$)$_2$-phenyl and —(CH$_2$)$_3$-phenyl, wherein said phenyl is unsubstituted or substituted by two R$^5$ groups.

In one embodiment, the compound is a compound of Formula IAb** wherein L$^1$ is —SO$_2$—, R$^1$ is phenyl, wherein said phenyl is substituted by one R$^5$ group in the 2- or 4-position, wherein said R$^5$ is —Cl, L$^2$ is —NH—C(O)—NH— or —C(O)—NH— and R$^2$ is selected from the group consisting of —CH$_2$-phenyl, —(CH$_2$)$_2$-phenyl and —(CH$_2$)$_3$-phenyl, wherein said phenyl is unsubstituted or substituted by two R$^5$ groups in 2- and 4-positions.

In one embodiment, the compound is a compound of Formula IAb** wherein L$^1$ is —SO$_2$—, R$^1$ is phenyl wherein said phenyl is substituted by one R$^5$ group in the 2- or 4-position, wherein said R$^5$ is —Cl, L$^2$ is —NH—C(O)—NH— or —C(O)—NH— and R$^2$ is selected from the group consisting of —CH$_2$-phenyl, —(CH$_2$)$_2$-phenyl and —(CH$_2$)$_3$-phenyl wherein said phenyl is unsubstituted or substituted by two halogens in 2- and 4-positions.

In one embodiment, the compound is a compound of Formula IAb** wherein L$^1$ is —SO$_2$—, R$^1$ is phenyl wherein said phenyl is substituted by one R$^5$ group in the 2- or 4-position, wherein said R$^5$ is —Cl, L$^2$ is —NH—C(O)—NH— or —C(O)—NH— and R$^2$ is selected from the group consisting of —CH$_2$-phenyl, —(CH$_2$)$_2$-phenyl and —(CH$_2$)$_3$-phenyl wherein said phenyl is unsubstituted or substituted by two —Cl in the 2- and 4-positions.

In one embodiment, the compound is a compound according to formula IAc,

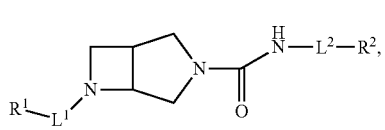

IAc wherein:
L$^1$ is a selected from the group consisting of bond, —(CH$_2$)$_{0-3}$—C(O)— and —(CH$_2$)$_{0-3}$—SO$_2$—;
L$^2$ is —(CH$_2$)$_{1-3}$—;
R$^1$ is phenyl or 5- or 6-membered heteroaryl, wherein said phenyl or heteroaryl is unsubstituted or substituted by one R$^5$ group;
R$^2$ is phenyl, wherein said phenyl is unsubstituted or substituted by two R$^5$ groups;
R$^4$ is hydrogen or lower alkyl; and
R$^5$ is halogen or —C(O)OR$^4$, or a
stereoisomer, tautomer or pharmaceutically acceptable salt thereof.

In one embodiment, the compound is a compound according to formula IAc wherein L$^1$ is selected from the group consisting of a bond, —C(O)—, and —SO$_2$—.

In one embodiment, the compound is a compound according to formula IAc wherein L$^1$ is selected from the group consisting of a bond, —C(O)—, and —SO$_2$— and R$^1$ is phenyl or pyrimidinyl, wherein said phenyl or pyrimidinyl is unsubstituted or substituted with one R$^5$ group.

In one embodiment, the compound is a compound according to formula IAc wherein L$^1$ is selected from the group consisting of a bond, —C(O)—, and —SO$_2$— and R$^1$ is phenyl or pyrimidinyl wherein said phenyl or pyrimidinyl is unsubstituted or substituted with one R$^5$ group in the 4-position.

In one embodiment, the compound is a compound according to formula IAc wherein $L^1$ is selected from the group consisting of a bond, —C(O)—, and —SO$_2$—, and $R^1$ is phenyl or pyrimidinyl wherein said phenyl or pyrimidinyl is unsubstituted or substituted with one $R^5$ group in the 4-position, wherein said $R^5$ is —C(O)OR$^4$.

In one embodiment, the compound is a compound according to formula IAc wherein $L^1$ is selected from the group consisting of a bond, —C(O)—, and —SO$_2$—, and $R^1$ is phenyl or pyrimidinyl wherein said phenyl or pyrimidinyl is unsubstituted or substituted with one $R^5$ group in the 4-position, wherein said $R^5$ is —C(O)OH.

In one embodiment, the compound is a compound according to formula IAc wherein $L^1$ is selected from the group consisting of a bond, —C(O)—, and —SO$_2$—$R^1$ is phenyl or pyrimidinyl wherein said phenyl or pyrimidinyl is unsubstituted or substituted with one $R^5$ group in the 4-position wherein said $R^5$ is —C(O)OH and $L^2$ is —CH$_2$—.

In one embodiment, the compound is a compound according to formula IAc wherein $L^1$ is selected from the group consisting of a bond, —C(O)—, and —SO$_2$—, $R^1$ is phenyl or pyrimidinyl wherein said phenyl or pyrimidinyl is unsubstituted or substituted with one $R^5$ group in the 4-position wherein said $R^5$ is —C(O)OH, $L^2$ is —CH$_2$— and $R^2$ is phenyl wherein said phenyl is substituted by two $R^5$ groups.

In one embodiment, the compound is a compound according to formula IAc wherein $L^1$ is selected from the group consisting of a bond, —C(O)—, and —SO$_2$—, $R^1$ is phenyl or pyrimidinyl, wherein said phenyl or pyrimidinyl is unsubstituted or substituted with one $R^5$ group in the 4-position, wherein said $R^5$ is —C(O)OH, $L^2$ is —CH$_2$— and $R^2$ is phenyl wherein said phenyl is substituted by two $R^5$ groups in the 2-position and 4-positions.

In one embodiment, the compound is a compound according to formula IAc wherein $L^1$ is selected from the group consisting of a bond, —C(O)—, and —SO$_2$—, $R^1$ is phenyl or pyrimidinyl wherein said phenyl or pyrimidinyl is unsubstituted or substituted with one $R^5$ group in the 4-position, wherein said $R^5$ is —C(O)OH, $L^2$ is —CH$_2$— and $R^2$ is phenyl wherein said phenyl is substituted by two halogen in the 2-position and the 4-position.

In one embodiment, the compound is a compound according to formula IAc wherein $L^1$ is selected from the group consisting of a bond, —C(O)—, and —SO$_2$—, $R^1$ is phenyl or pyrimidinyl wherein said phenyl or pyrimidinyl is unsubstituted or substituted with one $R^5$ group in the 4-position, wherein said $R^5$ is —C(O)OH, $L^2$ is —CH$_2$— and $R^2$ is phenyl wherein said phenyl is substituted by two —Cl in the 2-position and the 4-position.

Further it is to be understood that every embodiment relating to a specific residue A, $R^1$, $R^2$, $L^1$ and $L^2$ as disclosed herein may be combined with any other embodiment relating to another residue A, $R^1$, $R^2$, $L^1$ and $L^2$ as disclosed herein.

The application provides a compound of Formula I selected from the group consisting of:
6-Benzoyl-2,6-diaza-spiro[3.3]heptane-2-carboxylic acid 2,4-dichloro-benzylamide;
4-[6-(2,4-Dichloro-benzylcarbamoyl)-2,6-diaza-spiro[3.3]hept-2-yl]-benzoic acid;
6-(2,4-Dichloro-benzenesulfonyl)-2,6-diaza-spiro[3.3]heptane-2-carboxylic acid benzylamide;
6-Pyrimidin-2-yl-2,6-diaza-spiro[3.3]heptane-2-carboxylic acid 2,4-dichloro-benzylamide;
N-(2,4-Dichlorobenzyl)-1-(4-fluorophenylsulfonyl)-1,6-diazaspiro[3.3]heptane-6-carboxamide;
6-(4-Chlorophenylsulfonyl)-N-(2,4-dichlorobenzyl)-1,6-diazaspiro[3.3]heptane-1-carboxamide;
N-(2,4-Dichlorobenzyl)-1-(pyrimidin-2-yl)-1,6-diazaspiro[3.3]heptane-6-carboxamide;
Benzyl-1,6-diaza-spiro[3.3]heptane-6-carboxylic acid (3-phenyl-propyl)-amide;
1-(4-Chloro-benzenesulfonyl)-1,6-diaza-spiro[3.3]heptane-6-carboxylic acid (3-phenyl-propyl)-amide;
1-(4-Chloro-benzenesulfonyl)-1,6-diaza-spiro[3.3]heptane-6-carboxylic acid adamantan-1-ylamide;
1-(4-Chloro-benzenesulfonyl)-1,6-diaza-spiro[3.3]heptane-6-carboxylic acid 2,4-dichloro-benzylamide;
1-(4-Chloro-benzenesulfonyl)-1,6-diaza-spiro[3.3]heptane-6-carboxylic acid 2-trifluoromethoxy-benzylamide;
1-(2-trifluoromethyl-benzenesulfonyl)-1,6-diaza-spiro[3.3]heptane-6-carboxylic acid (3-phenyl-propyl)-amide;
(R)-2-(2-Chlorophenylsulfonyl)-N-(3-phenylpropyl)-2-azaspiro[3.3]heptane-5-carboxamide;
(S)-2-(2-Chlorophenylsulfonyl)-N-(3-phenylpropyl)-2-azaspiro[3.3]heptane-5-carboxamide;
(R)-1-(2-(4-Chlorophenylsulfonyl)-2-azaspiro[3.3]heptan-5-yl)-3-(2,4-dichlorobenzyl)urea;
(S)-1-(2-(4-Chlorophenylsulfonyl)-2-azaspiro[3.3]heptan-5-yl)-3-(2,4-dichlorobenzyl)urea;
rac-6-Benzoyl-3,6-diaza-bicyclo[3.2.0]heptane-3-carboxylic acid 2,4-dichloro-benzylamide;
rac-6-Benzenesulfonyl-3,6-diaza-bicyclo[3.2.0]heptane-3-carboxylic acid 2,4-dichloro-benzylamide;
rac-6-Pyrimidin-2-yl-3,6-diaza-bicyclo[3.2.0]heptane-3-carboxylic acid 2,4-dichloro-benzylamide; and
rac-4-[3-(2,4-Dichloro-benzylcarbamoyl)-3,6-diaza-bicyclo[3.2.0]hept-6-yl]-benzoic acid, or pharmaceutically acceptable salts thereof.

The application provides a compound of Formula I selected from the group consisting of:
6-Benzoyl-2,6-diaza-spiro[3.3]heptane-2-carboxylic acid 2,4-dichloro-benzylamide;
6-(2,4-Dichloro-benzenesulfonyl)-2,6-diaza-spiro[3.3]heptane-2-carboxylic acid benzylamide;
N-(2,4-Dichlorobenzyl)-1-(4-fluorophenylsulfonyl)-1,6-diazaspiro[3.3]heptane-6-carboxamide;
N-(2,4-Dichlorobenzyl)-1-(pyrimidin-2-yl)-1,6-diazaspiro[3.3]heptane-6-carboxamide;
1-(4-Chloro-benzenesulfonyl)-1,6-diaza-spiro[3.3]heptane-6-carboxylic acid 2-trifluoromethoxy-benzylamide;
(S)-2-(2-Chlorophenylsulfonyl)-N-(3-phenylpropyl)-2-azaspiro[3.3]heptane-5-carboxamide;
rac-6-Benzoyl-3,6-diaza-bicyclo[3.2.0]heptane-3-carboxylic acid 2,4-dichloro-benzylamide; and
rac-6-Benzenesulfonyl-3,6-diaza-bicyclo[3.2.0]heptane-3-carboxylic acid 2,4-dichloro-benzylamide; or pharmaceutically acceptable salts thereof The application provides a compound of Formula IAa selected from the group consisting of:
6-Benzoyl-2,6-diaza-spiro[3.3]heptane-2-carboxylic acid 2,4-dichloro-benzylamide;
4-[6-(2,4-Dichloro-benzylcarbamoyl)-2,6-diaza-spiro[3.3]hept-2-yl]-benzoic acid;
6-(2,4-Dichloro-benzenesulfonyl)-2,6-diaza-spiro[3.3]heptane-2-carboxylic acid benzylamide; and
6-Pyrimidin-2-yl-2,6-diaza-spiro[3.3]heptane-2-carboxylic acid 2,4-dichloro-benzylamide; or
pharmaceutically acceptable salts thereof.

The application provides a compound of Formula IAb* selected from the group consisting of:
N-(2,4-Dichlorobenzyl)-1-(4-fluorophenylsulfonyl)-1,6-diazaspiro[3.3]heptane-6-carboxamide;
6-(4-Chlorophenylsulfonyl)-N-(2,4-dichlorobenzyl)-1,6-diazaspiro[3.3]heptane-1-carboxamide;

N-(2,4-Dichlorobenzyl)-1-(pyrimidin-2-yl)-1,6-diazaspiro[3.3]heptane-6-carboxamide;

Benzyl-1,6-diaza-spiro[3.3]heptane-6-carboxylic acid (3-phenyl-propyl)-amide;

1-(4-Chloro-benzenesulfonyl)-1,6-diaza-spiro[3.3]heptane-6-carboxylic acid (3-phenyl-propyl)-amide;

1-(4-Chloro-benzenesulfonyl)-1,6-diaza-spiro[3.3]heptane-6-carboxylic acid adamantan-1-ylamide;

1-(4-Chloro-benzenesulfonyl)-1,6-diaza-spiro[3.3]heptane-6-carboxylic acid 2,4-dichloro-benzylamide;

1-(4-Chloro-benzenesulfonyl)-1,6-diaza-spiro[3.3]heptane-6-carboxylic acid 2-trifluoromethoxy-benzylamide; and 1-(2-trifluoromethyl-benzenesulfonyl)-1,6-diaza-spiro[3.3]heptane-6-carboxylic acid (3-phenyl-propyl)-amide; or pharmaceutically acceptable salts thereof The application provides a compound of Formula IAb** selected from the group consisting of:

(R)-2-(2-Chlorophenylsulfonyl)-N-(3-phenylpropyl)-2-azaspiro[3.3]heptane-5-carboxamide;

(S)-2-(2-Chlorophenylsulfonyl)-N-(3-phenylpropyl)-2-azaspiro[3.3]heptane-5-carboxamide;

(R)-1-(2-(4-Chlorophenylsulfonyl)-2-azaspiro[3.3]heptan-5-yl)-3-(2,4-dichlorobenzyl)urea; and (S)-1-(2-(4-Chlorophenylsulfonyl)-2-azaspiro[3.3]heptan-5-yl)-3-(2,4-dichlorobenzyl)urea; or pharmaceutically acceptable salts thereof.

The application provides a compound of Formula IAc selected from the group consisting of:

rac-6-Benzoyl-3,6-diaza-bicyclo[3.2.0]heptane-3-carboxylic acid 2,4-dichloro-benzylamide;

rac-6-Benzenesulfonyl-3,6-diaza-bicyclo[3.2.0]heptane-3-carboxylic acid 2,4-dichloro-benzylamide;

rac-6-Pyrimidin-2-yl-3,6-diaza-bicyclo[3.2.0]heptane-3-carboxylic acid 2,4-dichloro-benzylamide; and rac-4-[3-(2,4-Dichloro-benzylcarbamoyl)-3,6-diaza-bicyclo[3.2.0]hept-6-yl]-benzoic acid; or pharmaceutically acceptable salts thereof.

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of azetidine compounds according to generic Formula I:

TABLE I

| Exp. | Structure | Nomenclature | IC$_{50}$ [nM] |
|---|---|---|---|
| 1 | 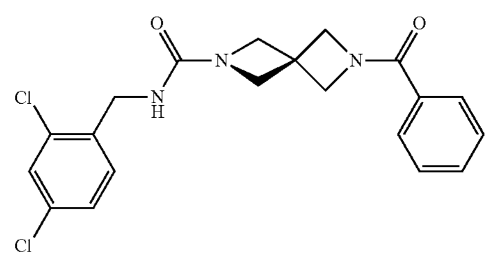 | 6-Benzoyl-2,6-diaza-spiro[3.3]heptane-2-carboxylic acid 2,4-dichloro-benzylamide | 241 |
| 2 | 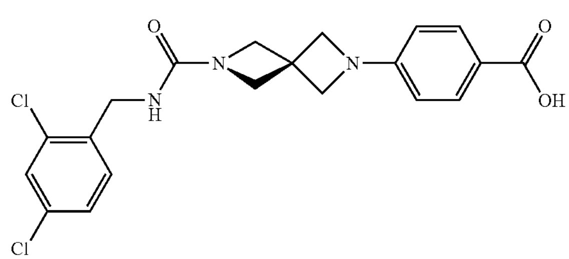 | 4-[6-(2,4-Dichloro-benzylcarbamoyl)-2,6-diaza-spiro[3.3]hept-2-yl]-benzoic acid | 1260 |
| 3 | 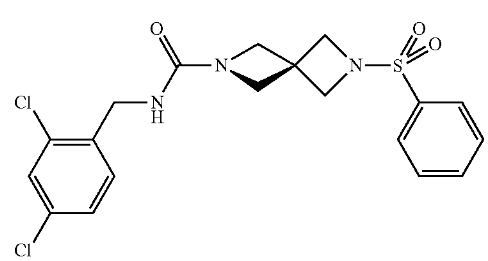 | 6-(2,4-Dichloro-benzenesulfonyl)-2,6-diaza-spiro[3.3]heptane-2-carboxylic acid benzylamide | 79 |

TABLE I-continued

| Exp. | Structure | Nomenclature | IC$_{50}$ [nM] |
|---|---|---|---|
| 4 | 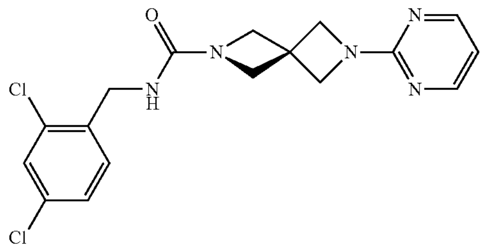 | 6-Pyrimidin-2-yl-2,6-diaza-spiro[3.3]heptane-2-carboxylic acid 2,4-dichloro-benzylamide | 2323 |
| 5 | 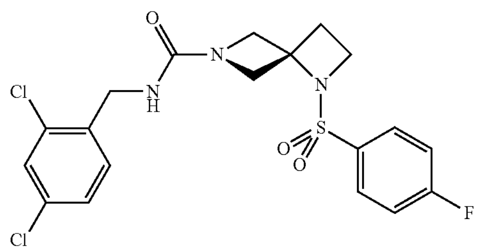 | N-(2,4-Dichlorobenzyl)-1-(4-fluorophenylsulfonyl)-1,6-diazaspiro[3.3]heptane-6-carboxamide | 284 |
| 6 | 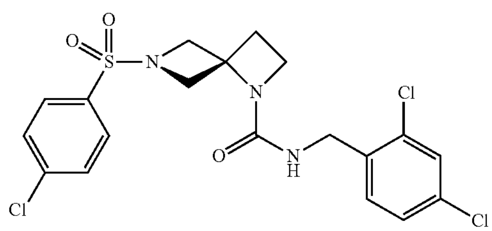 | 6-(4-Chlorophenylsulfonyl)-N-(2,4-dichlorobenzyl)-1,6-diazaspiro[3.3]heptane-1-carboxamide | 321 |
| 7 | 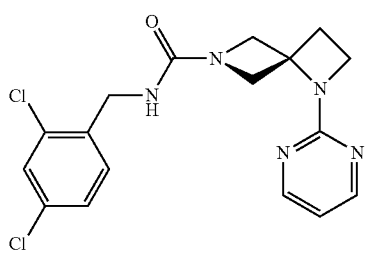 | N-(2,4-Dichlorobenzyl)-1-(pyrimidin-2-yl)-1,6-diazaspiro[3.3]heptane-6-carboxamide | 125 |
| 8 | 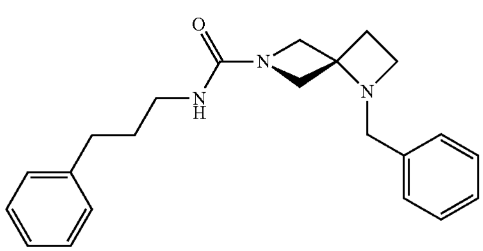 | Benzyl-1,6-diaza-spiro[3.3]heptane-6-carboxylic acid (3-phenyl-propyl)-amide | 1980 |
| 9 | 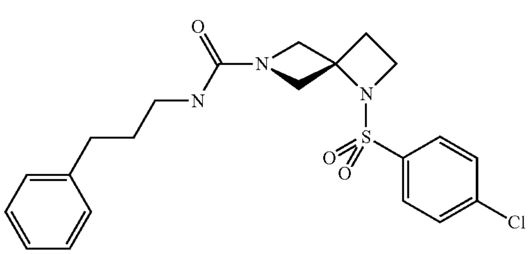 | 1-(4-Chloro-benzenesulfonyl)-1,6-diaza-spiro[3.3]heptane-6-carboxylic acid (3-phenyl-propyl)-amide | 1993 |

TABLE I-continued

| Exp. | Structure | Nomenclature | IC$_{50}$ [nM] |
|---|---|---|---|
| 10 | 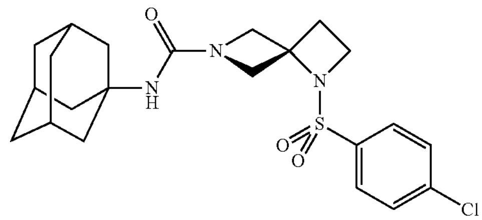 | 1-(4-Chloro-benzenesulfonyl)-1,6-diaza-spiro[3.3]heptane-6-carboxylic acid adamantan-1-ylamide | 2554 |
| 11 | 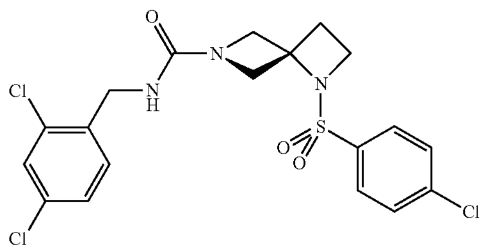 | 1-(4-Chloro-benzenesulfonyl)-1,6-diaza-spiro[3.3]heptane-6-carboxylic acid 2,4-dichloro-benzylamide | 640 |
| 12 | 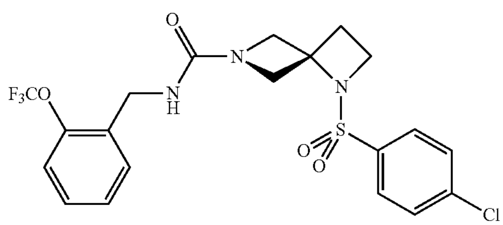 | 1-(4-Chloro-benzenesulfonyl)-1,6-diaza-spiro[3.3]heptane-6-carboxylic acid 2-trifluoromethoxy-benzylamide | 243 |
| 13 | 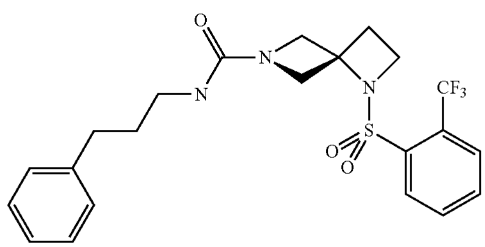 | 1-(2-trifluoromethyl-benzenesulfonyl)-1,6-diaza-spiro[3.3]heptane-6-carboxylic acid (3-phenyl-propyl)-amide | 476 |
| 14 | 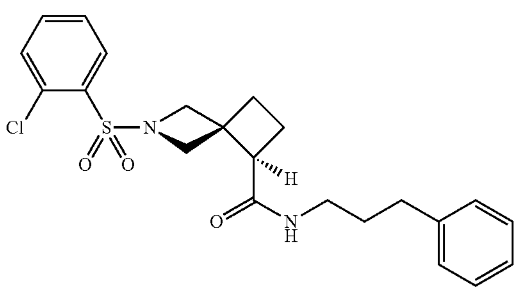 | (R)-2-(2-Chlorophenylsulfonyl)-N-(3-phenylpropyl)-2-azaspiro[3.3]heptane-5-carboxamide | 2792 |
| 15 | 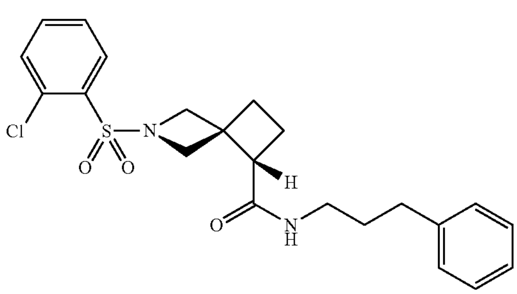 | (S)-2-(2-Chlorophenylsulfonyl)-N-(3-phenylpropyl)-2-azaspiro[3.3]heptane-5-carboxamide | 288 |

TABLE I-continued

| Exp. | Structure | Nomenclature | IC$_{50}$ [nM] |
|---|---|---|---|
| 16 | 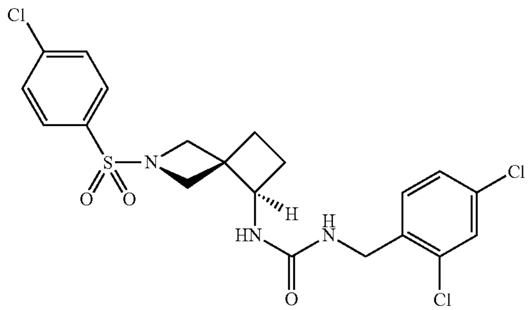 | (R)-1-(2-(4-Chlorophenylsulfonyl)-2-azaspiro[3.3]heptan-5-yl)-3-(2,4-dichlorobenzyl)urea | 2689 |
| 17 | 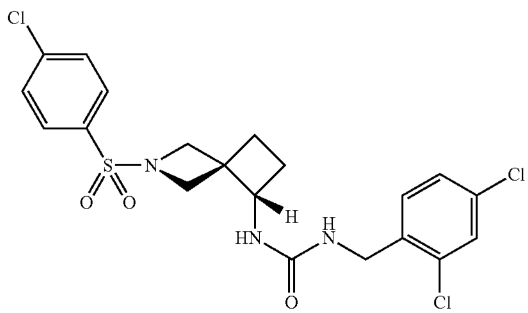 | (S)-1-(2-(4-Chlorophenylsulfonyl)-2-azaspiro[3.3]heptan-5-yl)-3-(2,4-dichlorobenzyl)urea | 678 |
| 18 | 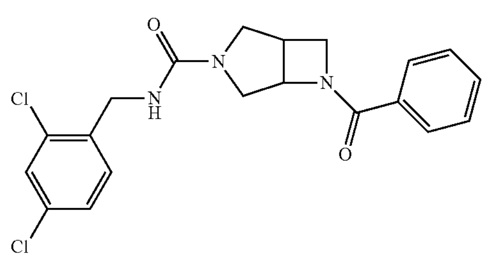 [SMILES: O=C(NCc1ccc(Cl)cc1Cl)N1CC2CN(C(=O)c3ccccc3)C2C1] | rac-6-Benzoyl-3,6-diaza-bicyclo[3.2.0]heptane-3-carboxylic acid 2,4-dichloro-benzylamide | 183 |
| 19 | 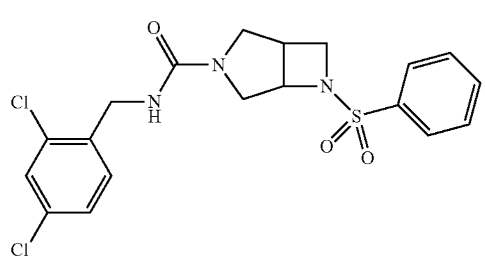 [SMILES: O=C(NCc1ccc(Cl)cc1Cl)N1CC2CN(S(=O)(=O)c3ccccc3)C2C1] | rac-6-Benzenesulfonyl-3,6-diaza-bicyclo[3.2.0]heptane-3-carboxylic acid 2,4-dichloro-benzylamide | 238 |
| 20 | 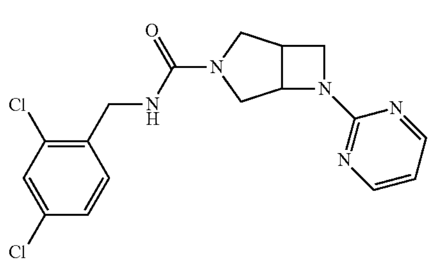 [SMILES: O=C(NCc1ccc(Cl)cc1Cl)N1CC2CN(c3ncccn3)C2C1] | rac-6-Pyrimidin-2-yl-3,6-diaza-bicyclo[3.2.0]heptane-3-carboxylic acid 2,4-dichloro-benzylamide | 361 |

TABLE I-continued

| Exp. | Structure | Nomenclature | IC$_{50}$ [nM] |
|---|---|---|---|
| 21 | (structure) | rac-4-[3-(2,4-Dichloro-benzylcarbamoyl)-3,6-diaza-bicyclo[3.2.0]hept-6-yl]-benzoic acid | 351 |

Synthesis of sEH Inhibitor Compounds

Any suitable materials known to those of skill can be utilized in carrying out the present invention. However, preferred materials and methods are described herein. Materials, reagents and the like to which reference are made in the following description and examples are obtainable from commercial sources, unless otherwise noted.

The preparation of compounds of the present invention may be carried out in sequential or convergent synthetic routes. Syntheses of the compounds of the invention are shown in the following schemes. For a more detailed description of the individual reaction steps, see the Examples section below.

It convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity the sequence of reaction steps can be freely altered.

In each of the schemes it may be advantageous to separate reaction products from one another and/or from starting materials. Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Enantiomers can also be separated by use of a chiral HPLC column.

A single stereoisomer, e.g. an enantiomer, substantially free of its stereoisomer may further be obtained by resolution of the racemic mixture using a method such as formation of diastereomers using optically active resolving agents (Eliel, E. and Wilen, S., *Stereochemistry of Organic Compounds*, John Wiley & Sons, Inc., New York, 1994; Lochmuller, C. H., *J. Chromatogr.*, 113(3):283-302 (1975)). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: *Drug Stereochemistry, Analytical Methods and Pharmacology*, Irving W. Wainer, Ed., Marcel Dekker, Inc., New York (1993).

Diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, the substrate to be resolved is reacted with one enantiomer of a chiral compound to form a diastereomeric pair (Eliel, E. and Wilen, S., *Stereochemistry of Organic Compounds*, John Wiley & Sons, Inc., New York, 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g. (−) menthyl chloroformate in the presence of base, or Mosher ester, α-methoxy-α-(trifluoromethyl)phenyl acetate (Jacob, *J. Org. Chem.* 47:4165 (1982)), of the racemic mixture, and analyzing the NMR spectrum for the presence of the two atropisomeric enantiomers or diastereomers. By method (3), a racemic mixture of two enantiomers can be separated by chromatography using a chiral stationary phase (*Chiral Liquid Chromatography* W. J. Lough, Ed., Chapman and Hall, New York, (1989); Okamoto, *J. of Chromatogr.* 513:375-378 (1990)). Enriched or purified enantiomers can be distinguished by methods used to distinguish other chiral molecules with asymmetric carbon atoms, such as optical rotation and circular dichroism.

General Schemes

The present compounds of Formulae I, IAa, IAb*, IAb** and IAc, stereoisomers, tautomers or pharmaceutically acceptable salts thereof may be prepared by methods known in the art, for example, by processes described below, which process comprises reacting a compound of Formulae II to VI

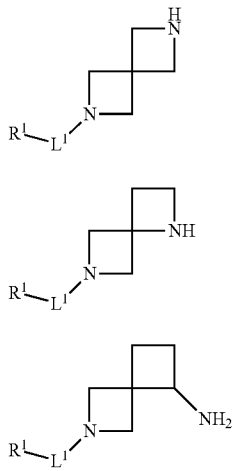

II

III

IV

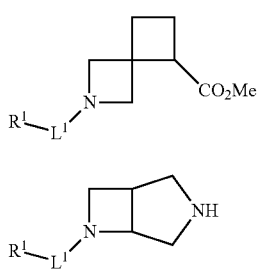

V

VI with a chemical of Formulae VII to X

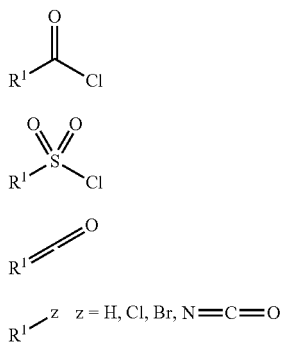

VII

VIII

IX

X   z = H, Cl, Br, N=C=O in the presence of a base and in addition for chemical of Formula X eventually in the presence of a suitable catalyst to a compound of Formulae I, IAa, IAb*, IAb** or IAc

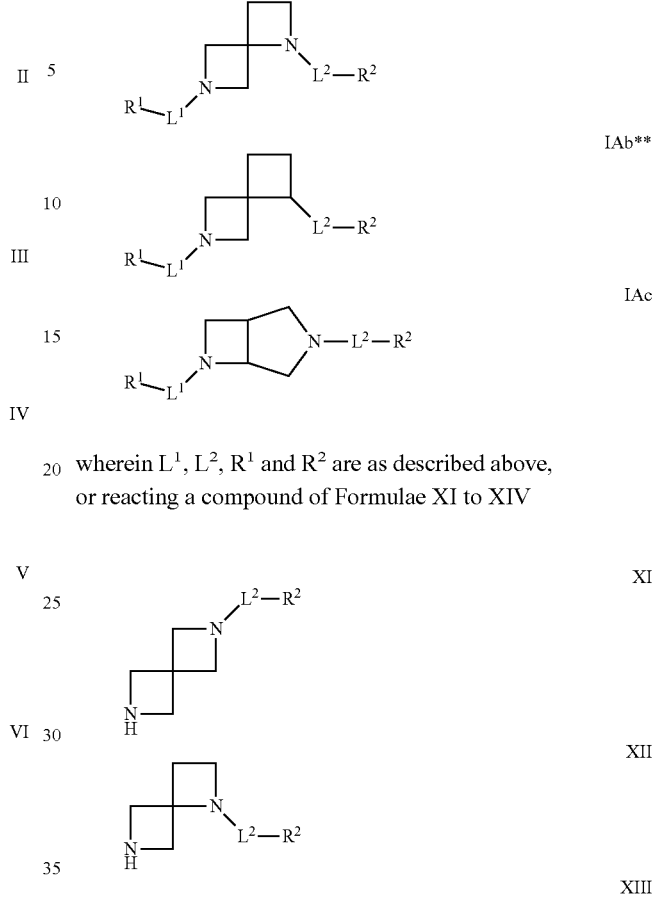

IAa

IAb*

IAb**

IAc wherein $L^1$, $L^2$, $R^1$ and $R^2$ are as described above, or reacting a compound of Formulae XI to XIV

XI

XII

XIII

XIV with a chemical of Formulae VII to IX or XV

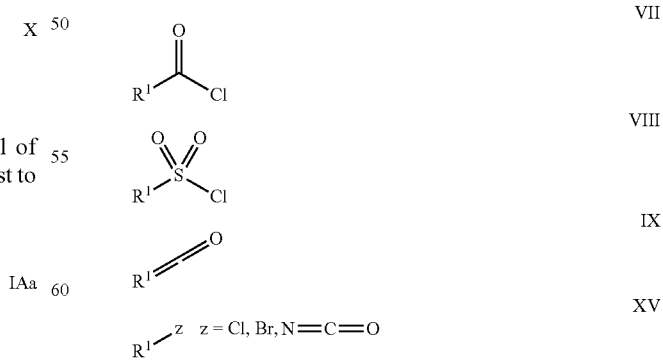

VII

VIII

IX

XV   z = Cl, Br, N=C=O in the presence of a base and in addition for a chemical of Formula XV eventually in the presence of a suitable catalyst to a compound of Formulae I, IAa, IAb*, IAb** or IAc

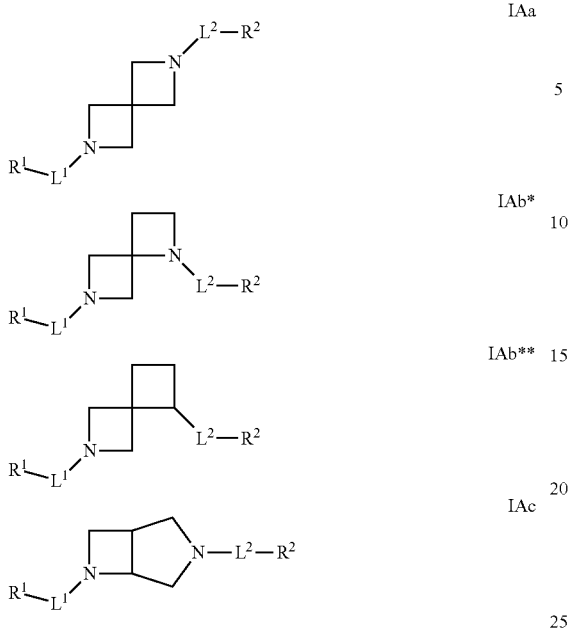

IAa

IAb*

IAb**

IAc wherein $L^1$, $L^2$, $R^1$ and $R^2$ are as described above, and, if desired, converting a compound of Formulae I, IAa, IAb*, IAb** or IAc into a pharmaceutically acceptable salt.

The following schemes describe the process for preparation of compounds of Formulae I, IAa, IAb*, IAb** or IAc in more detail. The starting materials of the following formulas are known compounds or may be prepared according to methods known in the art.

Scheme 1
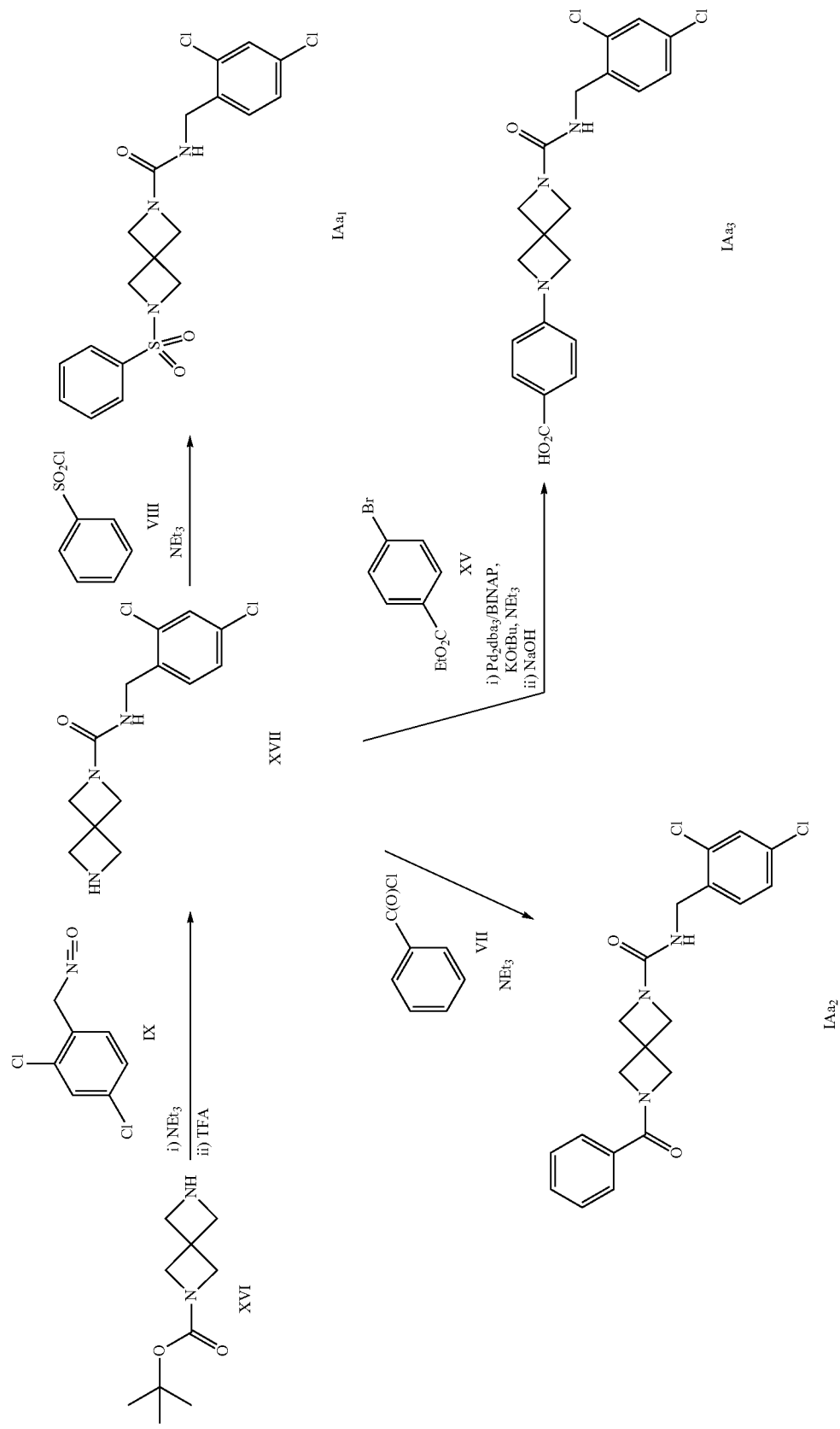

According to scheme 1, compounds of Formula IAa may be prepared as follows:

To a stirred solution of 6-(tert-butoxycarbonyl)-2,6-diaza-spiro[3.3]heptane, Formula XVI, in a suitable solvent, e.g. dichloromethane, is added a suitable base, e.g. triethylamine, followed by an isocyanate of Formula IX and the mixture is stirred at ambient or elevated temperature. The resulting product is then reacted with an acid, e.g. trifluoroacid, in a suitable solvent, e.g. dichloromethane, to obtain as urea of Formula XVII 2,6-diaza-spiro[3.3]heptane-2-carboxylic acid 2,4-dichloro-benzylamide. This compound XVII is converted into the final product of Formula IAa either by reacting amine XVII in a suitable solvent, e.g. dichloromethane, with a sulfonylchloride of Formula VIII in the presence of a suitable base, e.g. triethylamine, at ambient or elevated temperature or by reacting amine XVII in a suitable solvent, e.g. dichloromethane, with a carbonyl chloride of Formula VII in the presence of a suitable base, e.g. triethylamine, at ambient or elevated temperature or by reacting amine XVII in a suitable solvent, e.g. toluene, with an aryl bromide of Formula XV in the presence of a catalyst, e.g. Pd$_2$dba$_3$/BINAP, and suitable bases, e.g. triethylamine and potassium tert-butylate, at elevated temperature followed by a saponification reaction with a suitable agent, e.g. aqueous sodium hydroxide, in a suitable solvent, e.g. methanol or tetrahydrofuran, at ambient or elevated temperature.

Scheme 2

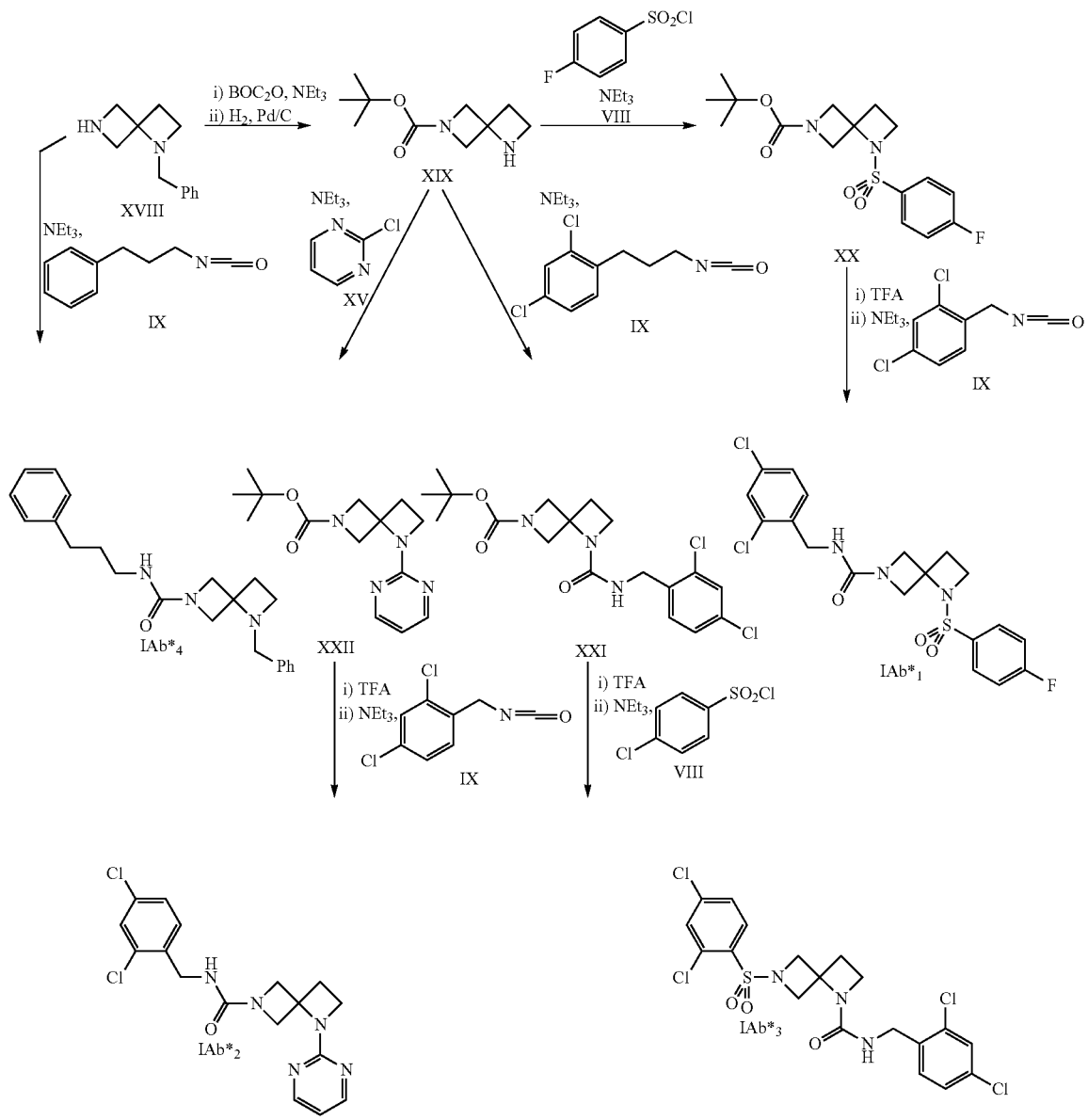

According to scheme 2, compounds of Formula IAb* may be prepared as follows:

To a stirred solution of 1-benzyl-1,6-diaza-spiro[3.3]heptane, Formula XVIII, in a suitable solvent, e.g. dichloromethane, is added a suitable base, e.g. triethylamine, followed by an isocyanate of Formula IX and the mixture is stirred at ambient or elevated temperature. Alternatively, 1-benzyl-1,6-diaza-spiro[3.3]heptane, Formula XVIII, is treated in a suitable solvent, e.g. methanol, with a suitable base, e.g. triethylamine, followed by BOC₂O and the mixture is stirred at ambient or elevated temperature. Hydrogenation of the resulting product in a suitable solvent, e.g. methanol, in presence of a suitable catalyst, e.g. palladium on charcoal, at ambient temperature affords amine XIX which can be further transformed by reacting with a sulfonylchloride of Formula VIII in the presence of a suitable base, e.g. triethylamine, in a suitable solvent, e.g. dichloromethane, at ambient or elevated temperature into sulphonamide of Formula XX which is then reacted with an acid, e.g. trifluoroacid, in a suitable solvent, e.g. dichloromethane, followed by a reaction in a suitable solvent, e.g. dichloromethane, with a suitable base, e.g. triethylamine, and an isocyanate of Formula IX at ambient or elevated temperature to obtain a final product of Formula IAb*. Amine XIX is converted into urea of formula XXI by reacting in a suitable solvent, e.g. dichloromethane, with a suitable base, e.g. triethylamine, and an isocyanate of formula IX at ambient or elevated temperature which is then further converted into a final product of Formula IAb* by reacting with an acid, e.g. trifluoroacid, in a suitable solvent, e.g. dichloromethane, followed by a reaction in a suitable solvent, e.g. dichloromethane, with a suitable base, e.g. triethylamine, and a sulfonylchloride of Formula VIII at ambient or elevated temperature. Amine XIX is converted into intermediate XXII by reacting in a suitable solvent, e.g. methanol, with a suitable base, e.g. triethylamine, and 2-chloropyrimidine of Formula XV at elevated temperature which then is transformed into a final product of Formula IAb* by reacting with an acid, e.g. trifluoroacid, in a suitable solvent, e.g. dichloromethane, followed by a reaction in a suitable solvent, e.g. dichloromethane, with a suitable base, e.g. triethylamine, and an isocyanate of Formula IX at ambient or elevated temperature.

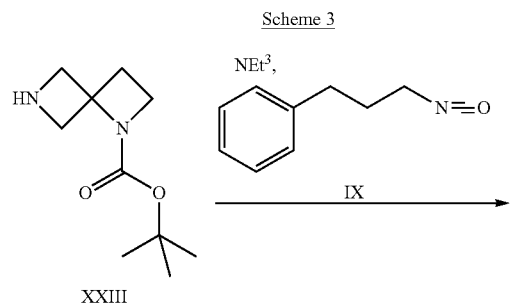

Scheme 3

According to scheme 3, compounds of Formula IAb* may be prepared as follows:

To a stirred solution of 1-(tert-butoxycarbonyl)-1,6-diaza-spiro[3.3]heptane, Formula XXIII, in a suitable solvent, e.g. dichloromethane, is added a suitable base, e.g. triethylamine, followed by an isocyanate of Formula IX and the mixture is stirred at ambient or elevated temperature to obtain an urea of Formula XXIV which then is transformed into a final product of Formula IAb* by reacting with an acid, e.g. trifluoroacid, in a suitable solvent, e.g. dichloromethane, followed by a reaction in a suitable solvent, e.g. dichloromethane, with a suitable base, e.g. triethylamine, and a sulfonylchloride of Formula VIII at ambient or elevated temperature.

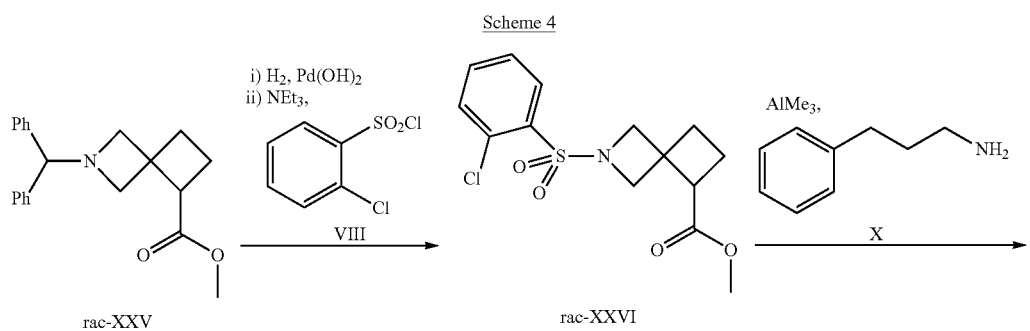

Scheme 4

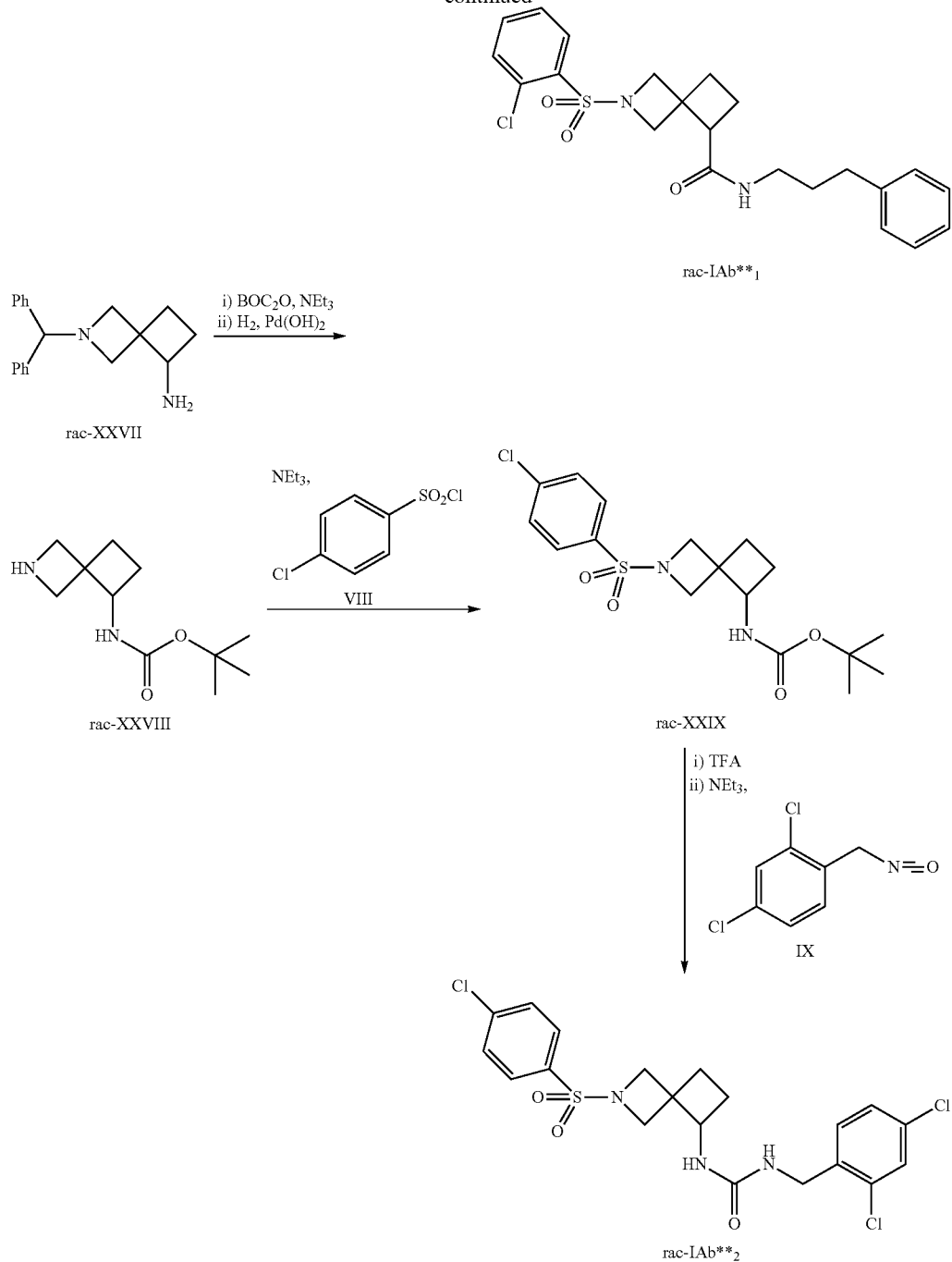

According to scheme 4, compounds of Formula rac-IAb** may be prepared as follows:

Hydrogenation of (R,S)-methyl 2-benzhydryl-2-azaspiro [3.3]heptane-5-carboxylate, Formula rac-XXV, in a suitable solvent, e.g. methanol, in presence of a suitable catalyst, e.g. palladium hydroxide, at ambient temperature affords followed by a reaction in a suitable solvent, e.g. dichloromethane, with a suitable base, e.g. triethylamine, and a sulfonylchloride of Formula VIII at ambient or elevated temperature affords the intermediate ester of Formula rac-XXVI which is treated with an amine of Formula X in presence of trimethylaluminium in a suitable solvent, e.g. dioxane, at elevated temperature to obtain a final product of Formula rac-IAb**.

Amine rac-XXVII is treated in a suitable solvent, e.g. methanol, with a suitable base, e.g. triethylamine, followed by BOC₂O and the mixture is stirred at ambient or elevated temperature followed by hydrogenation in a suitable solvent, e.g. methanol, in presence of a suitable catalyst, e.g. palladium hydroxide, at ambient temperature to afford the intermediate amine of Formula rac-XXVIII which is further transformed into a sulfonamide of Formula rac-XXIX by a reaction in a suitable solvent, e.g. dichloromethane, with a suitable base, e.g. triethylamine, and a sulfonylchloride of Formula VIII at ambient or elevated temperature. Final product of Formula rac-IAb** is then obtained by reacting with an acid, e.g. trifluoroacid, in a suitable solvent, e.g. dichloromethane, followed by a reaction in a suitable solvent, e.g. dichloromethane, with a suitable base, e.g. triethylamine, and an isocyanate of Formula IX at ambient or elevated temperature.

Separation of final compounds rac-IAb into their enantiomers IAb is accomplished by chiral HPLC.

Scheme 5
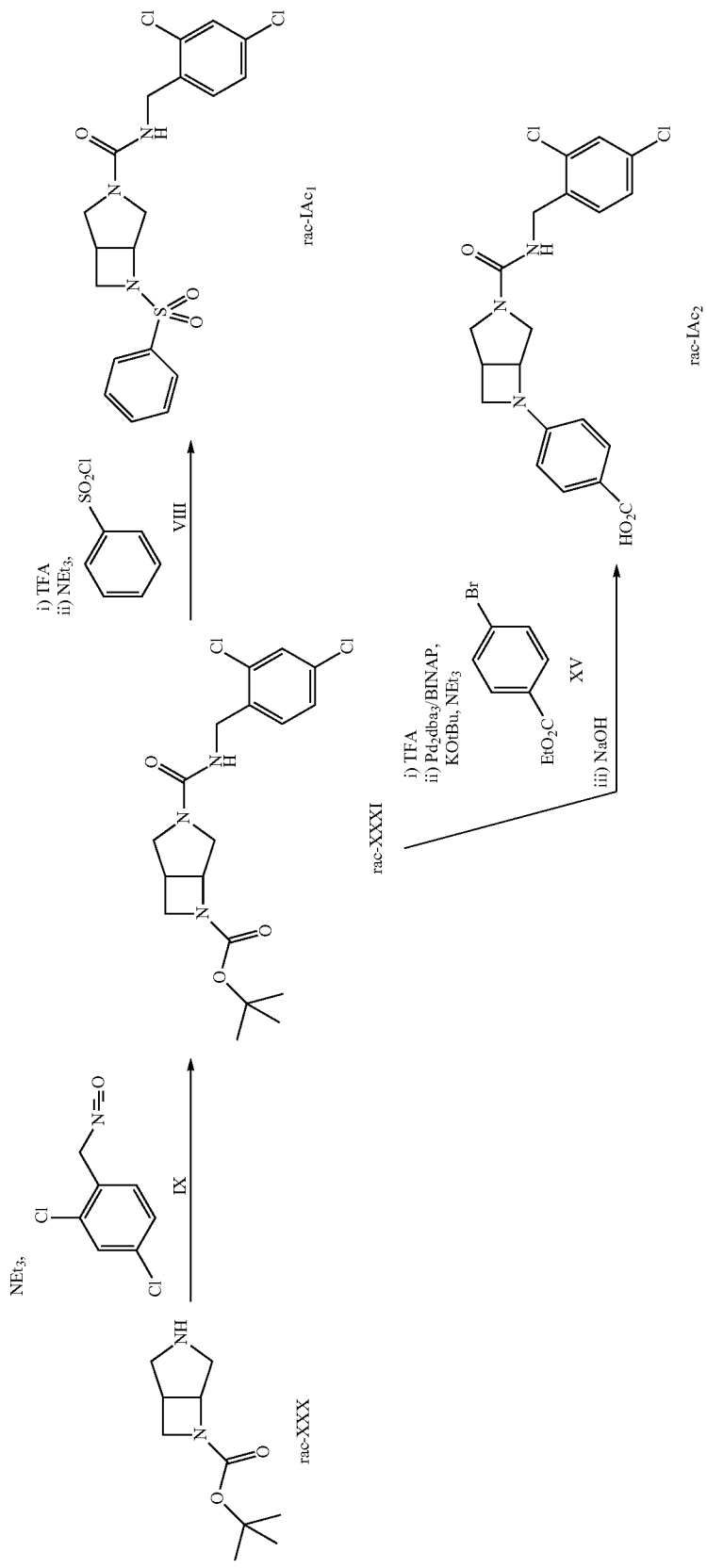

According to scheme 5, compounds of Formula rac-IAc may be prepared as follows:

To a stirred solution of rac-3,6-diaza-bicyclo[3.2.0]heptane-6-carboxylic acid tert-butyl ester, Formula rac-XXX, in a suitable solvent, e.g. dichloromethane, is added a suitable base, e.g. triethylamine, followed by an isocyanate of Formula IX and the mixture is stirred at ambient or elevated temperature to obtain an urea of Formula rac-XXXI which then is transformed into a final product of Formula rac-IAc by reacting with an acid, e.g. trifluoroacid, in a suitable solvent, e.g. dichloromethane, followed by either a reaction in a suitable solvent, e.g. dichloromethane, with a suitable base, e.g. triethylamine, and a sulfonylchloride of Formula VIII at ambient or elevated temperature or by a reaction in a suitable solvent, e.g. toluene, with an aryl bromide of Formula XV in the presence of a catalyst, e.g. $Pd_2dba_3$/BINAP, and suitable bases, e.g. triethylamine and potassium tert-butylate, at elevated temperature followed by a saponification reaction with a suitable agent, e.g. aqueous sodium hydroxide, in a suitable solvent, e.g. methanol or tetrahydrofuran, at ambient or elevated temperature.

Separation of final compounds rac-IAc into their enantiomers IAc can be accomplished by chiral HPLC.

Pharmaceutical Compositions and Administration

Another embodiment provides pharmaceutical compositions or medicaments comprising a compound of the present invention, stereoisomers, tautomers or pharmaceutically acceptable salts thereof and a therapeutically inert carrier, diluent or excipient. In one example, compounds of the present invention may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends on the particular use and the concentration of compound, and can range anywhere from about 3 to about 8. In one example, a compound of the present invention is formulated in an acetate buffer, at pH 5. In another embodiment, the compounds of the present invention are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular patient being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit sEH activity. For example, such amount may be below the amount that is toxic to normal cells, or the patient as a whole.

In one example, the pharmaceutically effective amount of the compound of the invention administered parenterally per dose will be in the range of about 0.01-100 mg/kg per day. In another embodiment, oral unit dosage forms, such as tablets and capsules, contain from about 0.01-1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal, inhaled and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, aerosols, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An embodiment, therefore, includes a pharmaceutical composition comprising a compound of the present invention, stereoisomers, tautomers or pharmaceutically acceptable salts thereof. A further embodiment includes a pharmaceutical composition comprising a compound of the present invention, stereoisomers, tautomers, or pharmaceutically acceptable salts thereof, together with a pharmaceutically acceptable carrier or excipient. A further embodiment includes a pharmaceutical composition comprising a compound of the present invention, stereoisomers, tautomers, or pharmaceutically acceptable salts thereof, together with a pharmaceutically acceptable carrier.

Another embodiment includes a pharmaceutical composition comprising a compound of the present invention, stereoisomers, tautomers or pharmaceutically acceptable salts thereof for use in the treatment of a disease responsive to the levels of EETs.

Another embodiment includes a pharmaceutical composition comprising a compound of the present invention, stereoisomers, tautomers or pharmaceutically acceptable salts thereof, for use in the treatment of genitourinary disease states, pain diseases states, respiratory disease states, cardiovascular disease states, metabolic disease states, neurological disease states, immunological disease states, inflammatory disease states, cancer, nephropathy, stroke, endothelial dysfunction, prevention of ischemic events and end organ protection.

Another embodiment includes the use of a compound of the present invention, stereoisomers, tautomers or pharmaceutically acceptable salts thereof as therapeutically active substance.

Another embodiment includes the use of a compound of the present invention, stereoisomers, tautomers or pharmaceutically acceptable salts thereof for treating a diseases state responsive to the levels of EETs in a patient.

Another embodiment includes the use of a compound of the present invention, stereoisomers, tautomers or pharmaceutically acceptable salts thereof for treating genitourinary disease states, pain diseases states, respiratory disease states, cardiovascular disease states, metabolic disease states, neurological disease states, immunological disease states, inflammatory disease states, cancer, nephropathy, stroke, endothelial dysfunction, prevention of ischemic events and end organ protection.

Another embodiment includes the use of a compound of the present invention, stereoisomers, tautomers or pharmaceutically acceptable salts thereof in the preparation of a medicament for the treatment of a diseases state responsive to the levels of EETs in a patient.

Another embodiment includes the use of a compound of the present invention, stereoisomers, tautomers or pharmaceutically acceptable salts thereof in the preparation of a medicament for the treatment of genitourinary disease states, pain diseases states, respiratory disease states, cardiovascular disease states, metabolic disease states, neurological disease states, immunological disease states, inflammatory disease states, cancer, nephropathy, stroke, endothelial dysfunction, prevention of ischemic events and end organ protection.

Another embodiment includes a compound of the present invention, stereoisomers, tautomers or pharmaceutically acceptable salts thereof, for use in the treatment of a disease state responsive to the levels of EETs in a patient.

Another embodiment includes a compound of the present invention, stereoisomers, tautomers or pharmaceutically acceptable salts thereof, for use in the treatment of genitourinary disease states, pain diseases states, respiratory disease states, cardiovascular disease states, metabolic disease states, neurological disease states, immunological disease states, inflammatory disease states, cancer, nephropathy, stroke, endothelial dysfunction, prevention of ischemic events and end organ protection.

Another embodiment includes a method for the treatment of a disease state responsive to the levels of EETs in a patient, which method comprises administering an effective amount of a compound of the present invention, stereoisomers, tautomers or pharmaceutically acceptable salts thereof to a patient.

Another embodiment includes a method for the treatment of genitourinary disease states, pain diseases states, respiratory disease states, cardiovascular disease states, metabolic disease states, neurological disease states, immunological disease states, inflammatory disease states, cancer, nephropathy, stroke, endothelial dysfunction, prevention of ischemic events and end organ protection, which method comprises administering an effective amount of a compound of the present invention, stereoisomers, tautomers or pharmaceutically acceptable salts thereof to a patient.

In another embodiment, the compounds of the present invention, stereoisomers, tautomers or pharmaceutically acceptable salts thereof, are very suitable for use in the treatment of cardiovascular disease states, metabolic disease states, pain disease states, immunological disease states, inflammatory disease states, prevention of ischemic events and end organ protection.

In another embodiment, the compounds of the present invention, stereoisomers, tautomers or pharmaceutically acceptable salts thereof, are also very suitable for use in the treatment of cardiovascular disease states, metabolic disease states, pain disease states, immunological disease states and inflammatory disease states.

In another embodiment, the compound of the present invention, stereoisomers, tautomers or pharmaceutically acceptable salts thereof, are also very suitable for use in the treatment of cardiovascular disease states, metabolic disease states and inflammatory disease states.

EXAMPLES

Example 1

6-Benzoyl-2,6-diaza-spiro[3.3]heptane-2-carboxylic acid 2,4-dichloro-benzylamide

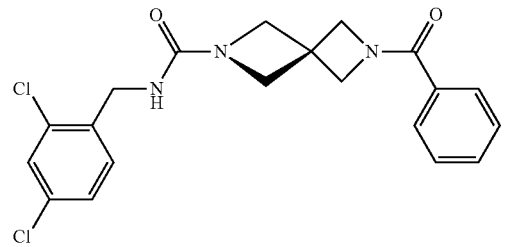

a) 6-(2,4-Dichloro-benzylcarbamoyl)-2,6-diaza-spiro[3.3]heptane-2-carboxylic acid tert-butyl ester

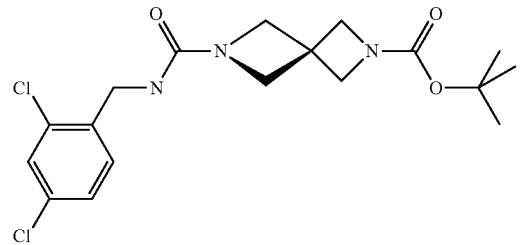

To a stirred solution of 6-(tert-butoxycarbonyl)-2,6-diazaspiro[3.3]heptane oxalate (200 mg, 1.01 mmol) in dichloromethane (10 mL) was added triethylamine (141 µl, 1.01 mmol) followed by 2,4-dichloro-1-(isocyanatomethyl)benzene (204 mg, 1.01 mmol). The reaction mixture was stirred at ambient temperature for 1 h. The crude reaction mixture was concentrated under reduced pressure. The residue was purified by chromatography (SiO$_2$; methanol:dichloromethane 0:1 to 1:9) to give the title compound (344 mg, 85%) as a white solid.

MS (EI) m/e: 400.0 (M+H)$^+$.

b) 2,6-Diaza-spiro[3.3]heptane-2-carboxylic acid 2,4-dichloro-benzylamide

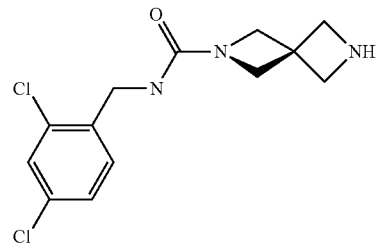

6-(2,4-Dichloro-benzylcarbamoyl)-2,6-diaza-spiro[3.3]heptane-2-carboxylic acid tert-butyl ester (20 mg, 50 µmol) and trifluoroacetic acid (740 mg, 6.49 mmol) were dissolved in dichloromethane (2 mL) and the reaction mixture was stirred for 30 min at ambient temperature. Concentration of the reaction mixture in vacuo afforded the title compound which was used without further purification.

c)
6-Benzoyl-2,6-diaza-spiro[3.3]heptane-2-carboxylic acid 2,4-dichloro-benzylamide 2,6-Diaza-spiro[3.3]heptane-2-carboxylic acid 2,4-dichloro-benzylamide (245 mg, 416 µmol) and triethylamine (200 mg, 198 mmol) were dissolved in dichloromethane (5 mL) followed by benzoyl chloride (70 mg, 499 µmol) and the reaction mixture was stirred for 1 h at ambient temperature. The crude reaction mixture was concentrated under reduced pressure. The residue was purified by chromatography (SiO$_2$; methanol:dichloromethane 0:1 to 1:19) to give the title compound (106 mg, 63%) as a colorless solid. MS (EI) m/e: 404.1 (M+H)+.

Example 2

4-[6-(2,4-Dichloro-benzylcarbamoyl)-2,6-diaza-spiro[3.3]hept-2-yl]-benzoic acid

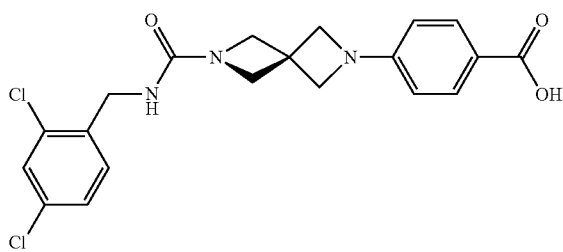

a) 4-[6-(2,4-Dichloro-benzylcarbamoyl)-2,6-diaza-spiro[3.3]hept-2-yl]-benzoic acid ethyl ester

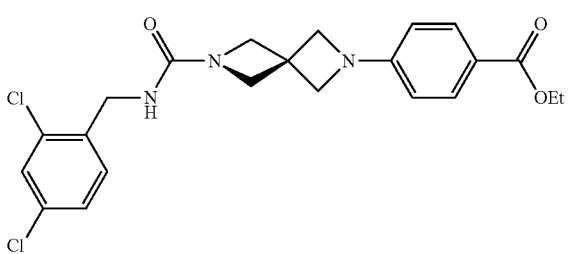

In analogy to the experimental procedure of example 21a) 2,6-diaza-spiro[3.3]heptane-2-carboxylic acid 2,4-dichloro-benzylamide instead of rac-3-(2,4-dichloro-benzylcarbamoyl)-3,6-diaza-bicyclo[3.2.0]heptane was converted into the title compound (44 mg, 23%) which was obtained as a colorless solid and used without further purification.

b) 6-(4-[6-(2,4-Dichloro-benzylcarbamoyl)-2,6-diaza-spiro[3.3]hept-2-yl]-benzoic acid In analogy to the experimental procedure of example 21b) 4-[6-(2,4-dichloro-benzylcarbamoyl)-2,6-diaza-spiro[3.3]hept-2-yl]-benzoic acid ethyl ester instead of rac-4-[3-(2,4-dichloro-benzylcarbamoyl)-3,6-diaza-bicyclo[3.2.0]hept-6-yl]-benzoic acid ethyl ester was converted into the title compound (27 mg, 65%) which was obtained as a white solid. MS (EI) m/e: 420.1 (M+H)+.

Example 3

6-(2,4-Dichloro-benzenesulfonyl)-2,6-diaza-spiro[3.3]heptane-2-carboxylic acid benzylamide

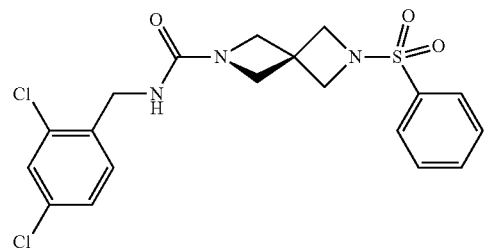

In analogy to the experimental procedure of example 1a) 2-benzenesulfonyl-2,6-diaza-spiro[3.3]heptane instead of 6-(tert-butoxycarbonyl)-2,6-diaza-spiro[3.3]heptane oxalate was converted using 2,4-dichloro-1-(isocyanatomethyl)benzene into the title compound (107 mg, 99%) which was obtained as a colorless solid. MS (EI) m/e: 440.1 (M+H)+.

Example 4

6-Pyrimidin-2-yl-2,6-diaza-spiro[3.3]heptane-2-carboxylic acid 2,4-dichloro-benzylamide

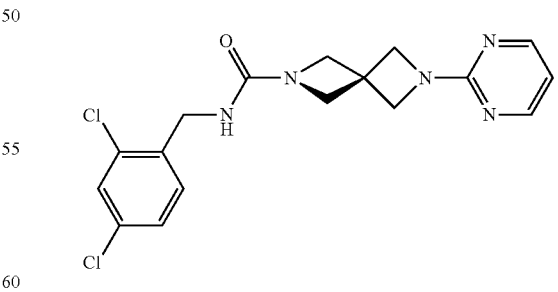

In analogy to the experimental procedure of example 1a) 2-Pyrimidin-2-yl-2,6-diaza-spiro[3.3]heptane instead of 6-(tert-butoxycarbonyl)-2,6-diaza-spiro[3.3]heptane oxalate was converted using 2,4-dichloro-1-(isocyanatomethyl)benzene into the title compound (32 mg, 62%) which was obtained as a colorless solid. MS (EI) m/e: 378.1 (M+H)+.

Example 5

N-(2,4-Dichlorobenzyl)-1-(4-fluorophenylsulfonyl)-1,6-diazaspiro[3.3]heptane-6-carboxamide

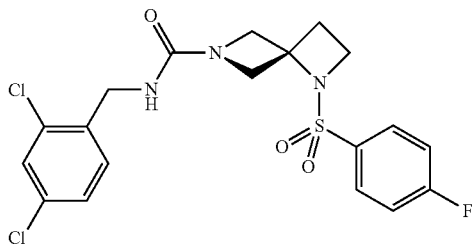

a) tert-Butyl 1-benzyl-1,6-diazaspiro[3.3]heptane-6-carboxylate

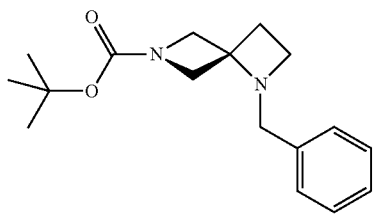

To a solution of 1-benzyl-1,6-diaza-spiro[3.3]heptane oxalate (1.55 g, 3.32 mmol) in methanol (10 mL) was added triethylamine (1.85 mL, 13.3 mmol). After 5 min, Boc$_2$O (1.7 mL, 7.31 mmol) was added and the reaction mixture was stirred at ambient temperature overnight, and was then concentrated under reduced pressure. Trituration with diethyl ether and concentration of the resulting filtrate afforded the title compound (1.79 g) as a yellow oil. MS (EI) m/e: 289.1 (M+H)$^+$.

b) 6-(tert-Butoxycarbonyl)-6-aza-1-azoniaspiro[3.3]heptane oxalate

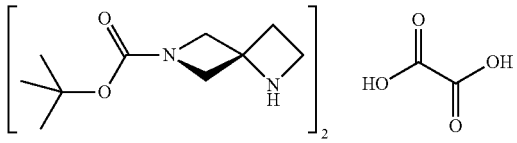

tert-Butyl 1-benzyl-1,6-diazaspiro[3.3]heptane-6-carboxylate (1.79 g, 6.21 mmol) was dissolved in methanol (33 mL), and Pd (10% on charcoal; 628 mg, 590 μmol) was added. A hydrogen atmosphere (balloon) was built up, and the mixture was stirred at ambient temperature for 24 h. Further Pd (10% on charcoal; 100 mg, 94 μmol, 0.015 equiv) was added and stirring under an hydrogen atmosphere was continued for another 24 h. The crude suspension was filtered over celite and the filter cake thoroughly washed with methanol, and the filtrate was concentrated under reduced pressure. To a solution of the residue in diethylether (140 mL) was added a solution of anhydrous oxalic acid (279 mg, 3.1 mmol) in ethanol (0.6 mL), upon which a precipitate formed immediately. The solid was filtered and dried under reduced pressure to give the title compound (1.18 g, 78%) as an amorphous colorless solid. MS (EI) m/e: 199.2 (M+H)$^+$.

c) tert-butyl 1-(4-fluorophenylsulfonyl)-1,6-diazaspiro[3.3]heptane-6-carboxylate

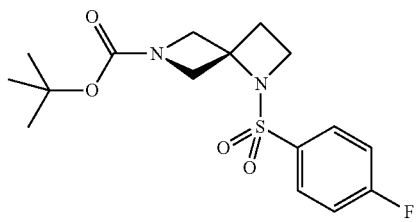

To a stirred solution of 6-(tert-butoxycarbonyl)-1,6-diazaspiro[3.3]heptane oxalate (350 mg, 719 μmol) in dichloromethane (6 mL) was added at 0° C. triethylamine (221 μl, 1.58 mmol) followed by 4-fluorobenzene-1-sulfonyl chloride (294 mg, 1.51 mmol). The reaction mixture was stirred at ambient temperature for 15 h. Further 4-fluorobenzene-1-sulfonyl chloride (100 mg, 0.51 mmol) and triethylamine (200 μl, 1.4 mmol) were added, the reaction mixture was stirred at ambient temperature for another 3 h. The reaction mixture was then diluted with dichloromethane 10 mL) and quenched with water (10 mL). The aqueous phase was extracted with CH$_2$Cl$_2$, and the combined organic phases were washed with brine, dried over sodium sulfate and concentrated under reduced pressure. The residue was purified by chromatography (SiO$_2$; heptane:ethyl acetate 2:1) to give the title compound (456 mg, 89%) as a colorless oil. MS (EI) m/e: 357.1 (M+H)$^+$.

d) N-(2,4-Dichlorobenzyl)-1-(4-fluorophenylsulfonyl)-1,6-diazaspiro[3.3]heptane-6-carboxamide To a solution of tert-butyl 1-(4-fluorophenylsulfonyl)-1,6-diazaspiro[3.3]heptane-6-carboxylate (452 mg, 1.27 mmol) in dichloromethane (8 mL) was added trifluoroacetic acid (489 μl, 6.34 mmol). After 2 h at ambient temperature, another amount of trifluoroacetic acid was added (300 μl, 3.89 mmol). The reaction mixture was stirred for 1.5 h at ambient temperature and concentrated under reduced pressure. The residue was partitioned in toluene (10 mL) and then concentrated, this procedure was repeated twice to give the unpurified amine (540 mg), which was used directly in the next step without further purification. To a solution of the obtained 1-(4-fluorophenylsulfonyl)-1,6-diazaspiro[3.3]heptanes in acetonitrile (10 mL) was added 2,4-dichloro-1-(isocyanatomethyl)benzene (216 μl, 1.47 mmol) followed by triethylamine (294 μl, 2.11 mmol) and the mixture was stirred for 1 h at ambient temperature. The solvent was evaporated in vacuo and the resulting solid was purified by chromatography (SiO$_2$; heptane:ethyl acetate 1:4 to dichloromethane/methanol/ammonia 95:4.5:0.5) to give the titled compound (530 mg, 91%) as colorless solid. HRMS (EI): 457.0431 (exact mass calculated for C$_{19}$H$_{17}$Cl$_2$FN$_3$O$_3$S ([M]$^+$)=457.0430).

Example 6

6-(4-Chlorophenylsulfonyl)-N-(2,4-dichlorobenzyl)-1,6-diazaspiro[3.3]heptane-1-carboxamide

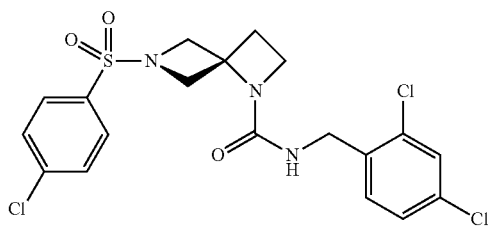

a) tert-Butyl 1-(2,4-dichlorobenzylcarbamoyl)-1,6-diazaspiro[3.3]heptane-6-carboxylate

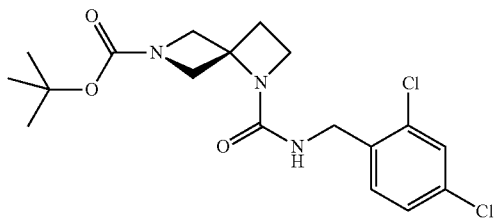

To a solution of 6-(tert-butoxycarbonyl)-1,6-diaza-spiro[3.3]heptane oxalate (350 mg, 719 μmol) in acetonitrile (5 mL) was added 2,4-dichloro-1-(isocyanatomethyl)benzene (291 mg, 1.44 mmol) followed by triethylamine (201 μl, 1.44 mmol) and the mixture was stirred overnight. Further 2,4-dichloro-1-(isocyanatomethyl)benzene (100 mg, 0.49 mmol) was added. After 1 hour at ambient temperature, the reaction was concentrated under reduced pressure. The residue was purified by chromatography (SiO$_2$; heptane:ethyl acetate 1:4) to give the title compound (378 mg, 65%) as a colorless foam. MS (EI) m/e: 400.2 (M+H)$^+$.

b) 6-(4-Chlorophenylsulfonyl)-N-(2,4-dichlorobenzyl)-1,6-diazaspiro[3.3]heptane-1-carboxamide To a solution of tert-butyl 1-(2,4-dichlorobenzylcarbamoyl)-1,6-diazaspiro[3.3]heptane-6-carboxylate (440 mg, 1.10 mmol) in dichloromethane (7 mL) was added TFA (593 μl, 7.7 mmol). After being stirred 2 h at ambient temperature, the reaction mixture was concentrated under reduced pressure. The residue was partitioned in toluene (10 mL) and then concentrated; this procedure was repeated twice to give the free amine (468 mg), which was used without further purification in the next step. To a solution of the previously obtained N-(2,4-dichlorobenzyl)-1,6-diazaspiro[3.3]heptane-1-carboxamide in dichloromethane (12 mL) was added at 0° C. triethylamine (217 μl, 1.56 mmol) followed by 4-chlorobenzene-1-sulfonyl chloride (329 mg, 1.56 mmol). The reaction mixture was left to warm to ambient temperature overnight, and was then diluted with dichloromethane (10 mL) and quenched with water (10 mL). The aqueous phase was extracted with dichloromethane and the combined organic phases were washed with brine, dried over sodium sulfate and were concentrated under reduced pressure. Purification by chromatography (SiO$_2$; heptane:ethyl acetate 1:4) afforded the title compound (445 mg, 85%) as a colorless solid. HRMS (EI): 473.0134 (exact mass calculated for C$_{19}$H$_{18}$Cl$_3$N$_3$O$_3$S ([M]$^+$)=473.0134).

Example 7

N-(2,4-Dichlorobenzyl)-1-(pyrimidin-2-yl)-1,6-diazaspiro[3.3]heptane-6-carboxamide

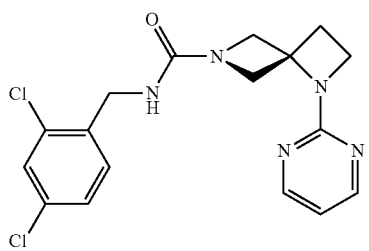

a) N-(2,4-Dichlorobenzyl)-1-(pyrimidin-2-yl)-1,6-diazaspiro[3.3]heptane-6-carboxamide

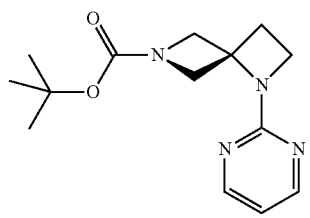

To a stirred solution of 6-(tert-butoxycarbonyl)-1,6-diazaspiro[3.3]heptane oxalate (350 mg, 719 μmol) in methanol (20 mL) was added 2-chloropyrimidine (181 mg, 1.58 mmol) and triethylamine (241 μL, 1.73 mmol). The reaction mixture was heated at reflux for 15 h. Further 2-chloropyrimidine (80 mg, 0.70 mmol) and triethylamine (100 μl, 0.71 mmol) were added, the reaction mixture was then heated at reflux for another 8 h. After addition of a spatula of tetrabutylammonium iodide the mixture was stirred at reflux for 60 h. The reaction mixture was then concentrated under reduced pressure, diluted with ethyl acetate and washed with aqueous sodium hydroxide (15%). The combined organic extracts were dried over sodium sulfate and concentrated under reduced pressure. This material was purified by chromatography (SiO$_2$; heptane:ethyl acetate 1:2) to give the title compound (293 mg, 73%) as a colorless oil. MS (EI) m/e: 277.2 ([M+H])$^+$.

b) N-(2,4-Dichlorobenzyl)-1-(pyrimidin-2-yl)-1,6-diazaspiro[3.3]heptane-6-carboxamide In analogy to the experimental procedure of example 5d) tert-butyl 1-(pyrimidin-2-yl)-1,6-diazaspiro[3.3]heptane-6-carboxylate instead of tert-butyl 1-(4-fluorophenylsulfonyl)-1,6-diazaspiro[3.3]heptane-6-carboxylate was converted into the title compound (181 mg, 45%) which was obtained as a colorless solid. HRMS (EI): 378.0876 (exact mass calculated for C$_{17}$H$_{17}$Cl$_2$N$_5$ ([M+H]$^+$)=378.0883).

Example 8

Benzyl-1,6-diaza-spiro[3.3]heptane-6-carboxylic acid (3-phenyl-propyl)-amide

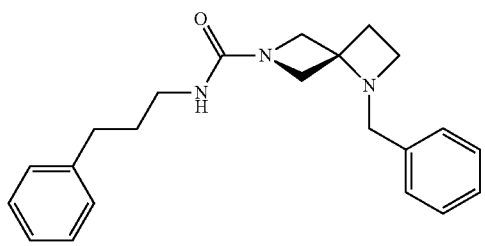

To a solution of 1-benzyl-1,6-diaza-spiro[3.3]heptane (41 mg, 217 μmol) in dichloromethane (2 mL) was added diisopropyl-ethyl-amine (112 mg, 868 μmol)) followed by (3-isocyanato-propyl)-benzene (84 mg, 521 μmol) and the reaction mixture was allowed to stir at ambient temperature for 16 h. After complete consumption of starting material the reaction mixture was diluted with dichloromethane and was washed successively with water and brine. The organic layer was dried over sodium sulfate and evaporated under reduced pressure. Purification by HPLC afforded the title compound (9 mg, 12%) as an off-white solid. MS m/e: 350 (M+H)+.

Example 9

1-(4-Chloro-benzenesulfonyl)-1,6-diaza-spiro[3.3]heptane-6-carboxylic acid (3-phenyl-propyl)-amide

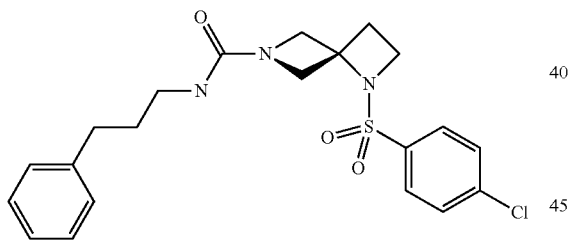

a) 6-(3-Phenyl-propylcarbamoyl)-1,6-diaza-spiro[3.3]heptane-1-carboxylic acid tert-butyl ester

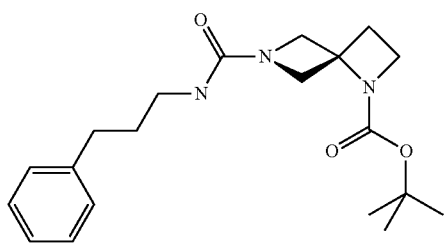

In analogy to the experimental procedure of example 8) 1,6-diaza-spiro[3.3]heptane-1-carboxylic acid tert-butyl ester instead of 1-benzyl-1,6-diaza-spiro[3.3]heptane was converted using (3-isocyanato-propyl)-benzene into the title compound which was used directly in the next step without further purification.

b) 1-(4-Chloro-benzenesulfonyl)-1,6-diaza-spiro[3.3]heptane-6-carboxylic acid (3-phenyl-propyl)-amide In analogy to the experimental procedure of example 6b) 6-(3-phenyl-propylcarbamoyl)-1,6-diaza-spiro[3.3]heptane-1-carboxylic acid tert-butyl ester instead of tert-butyl 1-(2,4-dichlorobenzylcarbamoyl)-1,6-diazaspiro[3.3]heptane-6-carboxylate was converted using 4-chlorobenzene-1-sulfonyl chloride into the title compound which was obtained as a colorless sticky solid (25 mg, 17%). MS m/e: 434 (M+H)+.

Example 10

1-(4-Chloro-benzenesulfonyl)-1,6-diaza-spiro[3.3]heptane-6-carboxylic acid adamantan-1-ylamide

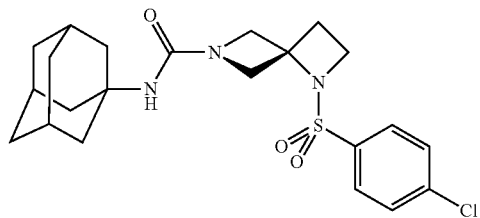

a) 6-(Adamantan-1-ylcarbamoyl)-1,6-diaza-spiro[3.3]heptane-1-carboxylic acid tert-butyl ester

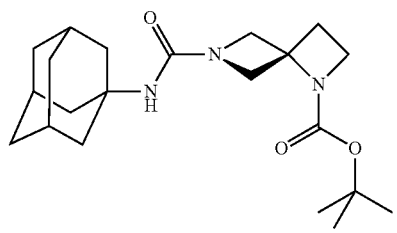

In analogy to the experimental procedure of example 8) 1,6-diaza-spiro[3.3]heptane-1-carboxylic acid tert-butyl ester instead of 1-benzyl-1,6-diaza-spiro[3.3]heptane was converted using 1-isocyanato-adamantane instead of (3-isocyanato-propyl)-benzene into the title compound which was used directly in the next step without further purification.

b) 1-(4-Chloro-benzenesulfonyl)-1,6-diaza-spiro[3.3]heptane-6-carboxylic acid adamantan-1-ylamide In analogy to the experimental procedure of example 6b) 6-(Adamantan-1-ylcarbamoyl)-1,6-diaza-spiro[3.3]heptane-1-carboxylic acid tert-butyl ester instead of tert-butyl 1-(2,4-dichlorobenzylcarbamoyl)-1,6-diazaspiro[3.3]heptane-6-carboxylate was converted using 4-chlorobenzene-1-sulfonyl chloride into the title compound which was obtained as an off-white sticky solid (29 mg, 35%). MS m/e: 450 (M+H)+.

Example 11

1-(4-Chloro-benzenesulfonyl)-1,6-diaza-spiro[3.3]heptane-6-carboxylic acid 2,4-dichloro-benzylamide

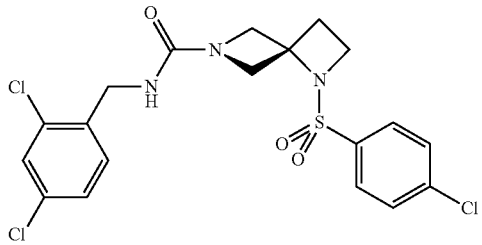

a) 6-(2,4-Dichloro-benzylcarbamoyl)-1,6-diaza-spiro[3.3]heptane-1-carboxylic acid tert-butyl ester

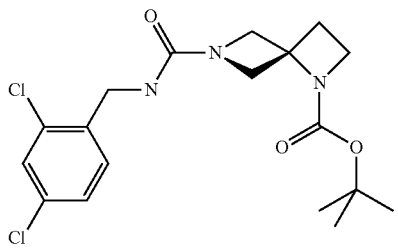

In analogy to the experimental procedure of example 8) 1,6-diaza-spiro[3.3]heptane-1-carboxylic acid tert-butyl ester instead of 1-benzyl-1,6-diaza-spiro[3.3]heptane was converted using 2,4-dichloro-1-isocyanatomethyl-benzene instead of (3-isocyanato-propyl)-benzene into the title compound which was used directly in the next step without further purification.

b) 1-(4-Chloro-benzenesulfonyl)-1,6-diaza-spiro[3.3]heptane-6-carboxylic acid 2,4-dichloro-benzylamide In analogy to the experimental procedure of example 6b) 6-(2,4-Dichloro-benzylcarbamoyl)-1,6-diaza-spiro[3.3]heptane-1-carboxylic acid tert-butyl ester instead of tert-butyl 1-(2,4-dichlorobenzylcarbamoyl)-1,6-diazaspiro[3.3]heptane-6-carboxylate was converted using 4-chlorobenzene-1-sulfonyl chloride into the title compound which was obtained as an off-white solid (41 mg, 23%). MS m/e: 474 (M+H)+.

Example 12

1-(4-Chloro-benzenesulfonyl)-1,6-diaza-spiro[3.3]heptane-6-carboxylic acid 2-trifluoromethoxy-benzylamide

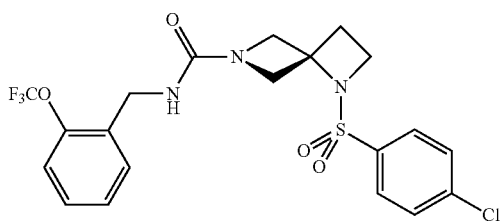

a) 6-(2-trifluoromethoxy-benzylcarbamoyl)-1,6-diaza-spiro[3.3]heptane-1-carboxylic acid tert-butyl ester

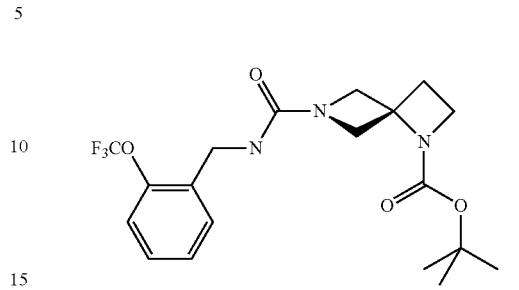

In analogy to the experimental procedure of example 8) 1,6-diaza-spiro[3.3]heptane-1-carboxylic acid tert-butyl ester instead of 1-benzyl-1,6-diaza-spiro[3.3]heptane was converted using 1-trifluoromethoxy-2-isocyanatomethyl-benzene instead of (3-isocyanato-propyl)-benzene into the title compound which was used directly in the next step without further purification.

b) 1-(4-Chloro-benzenesulfonyl)-1,6-diaza-spiro[3.3]heptane-6-carboxylic acid 2-trifluoromethoxy-benzylamide In analogy to the experimental procedure of example 6b) 6-(2-Chloro-benzylcarbamoyl)-1,6-diaza-spiro[3.3]heptane-1-carboxylic acid tert-butyl ester instead of tert-butyl 1-(2,4-dichlorobenzylcarbamoyl)-1,6-diazaspiro[3.3]heptane-6-carboxylate was converted using 4-chlorobenzene-1-sulfonyl chloride into the title compound which was obtained as an off-white solid (64 mg, 62%). MS m/e: 490 (M+H)+.

Example 13

1-(2-trifluoromethyl-benzenesulfonyl)-1,6-diaza-spiro[3.3]heptane-6-carboxylic acid (3-phenyl-propyl)-amide

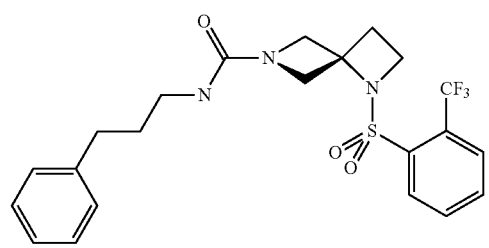

In analogy to the experimental procedure of example 6b) 6-(3-phenyl-propylcarbamoyl)-1,6-diaza-spiro[3.3]heptane-1-carboxylic acid tert-butyl ester instead of tert-butyl 1-(2,4-dichlorobenzylcarbamoyl)-1,6-diazaspiro[3.3]heptane-6-carboxylate was converted using 2-trifluoromethylbenzene-1-sulfonyl chloride instead of 4-chlorobenzene-1-sulfonyl chloride into the title compound which was obtained as an off-white solid (38 mg, 25%). MS m/e: 468 (M+H)+.

Example 14 and 15

(R)-2-(2-Chlorophenylsulfonyl)-N-(3-phenylpropyl)-2-azaspiro[3.3]heptane-5-carboxamide and (S)-2-(2-Chlorophenylsulfonyl)-N-(3-phenylpropyl)-2-azaspiro[3.3]heptane-5-carboxamide

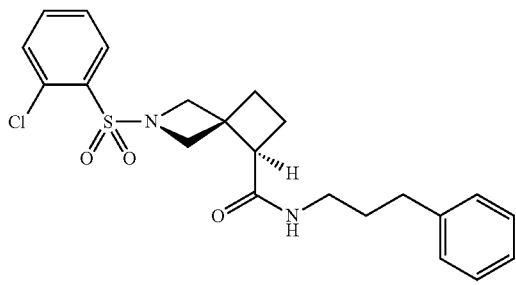

and

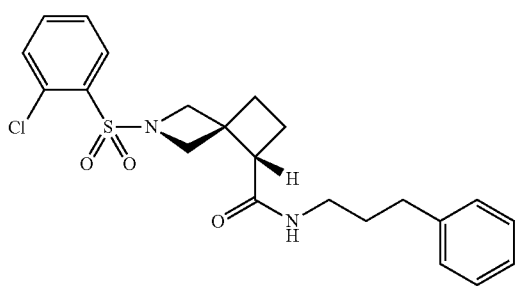

a) (R,S)-Methyl 2-(2-chlorophenylsulfonyl)-2-azaspiro[3.3]heptane-5-carboxylate

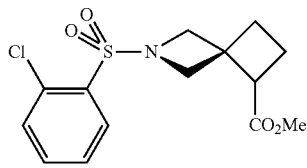

To a solution of (R,S)-methyl 2-benzhydryl-2-azaspiro[3.3]heptane-5-carboxylate (325 mg, 1.01 mmol) in methanol (15 mL), Pearlman's catalyst (20 wt. % loading, 142 mg, 202 µmol) was added at room temperature. A hydrogen atmosphere (balloon) was built up, and the mixture was stirred at ambient temperature for 60 h. Further Pearlman's catalyst (20 wt. % loading, 230 mg, 327 µmol) was added, and the mixture stirred for 5 h at ambient temperature under a hydrogen atmosphere. The crude suspension was filtered over celite and the filter cake thoroughly washed with methanol. The filtrate was concentrated under reduce pressure to give an oil which was used without further purification in the next step. To a solution of methyl 2-azaspiro[3.3]heptane-5-carboxylate in dichloromethane (6 mL) was added at 0° C. triethylamine (244 µl, 1.75 mmol) followed by 2-chlorobenzene-1-sulfonyl chloride (284 mg, 1.35 mmol). The reaction mixture was stirred at ambient temperature for 1 h, and was then diluted with dichloromethane and water. The aqueous phase was extracted with dichloromethane, and the combined organic extracts were washed with brine, dried over sodium sulfate, and concentrated under reduced pressure. The residue was purified by chromatography (SiO$_2$; heptane:ethyl acetate 2:1) to give the title compound as a colorless oil (112 mg, 34%). MS (EI) m/e: 330.0 ([M+H])$^+$.

b) (R,S)-2-(2-Chlorophenylsulfonyl)-N-(3-phenylpropyl)-2-azaspiro[3.3]heptane-5-carboxamide

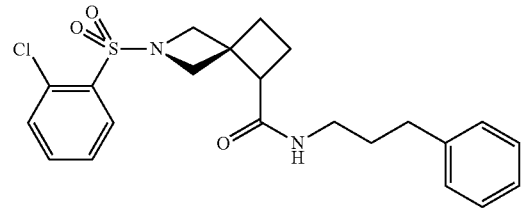

To a solution of 3-phenylpropan-1-amine (170 µl, 1.19 mmol) in dioxane (1.5 mL) was added dropwise trimethylaluminium (2M in heptanes; 594 µl, 1.19 mmol) under an atmosphere of nitrogen (cooling in a manner that the temperature was between 20-25° C.). After stirring for 1.5 h at ambient temperature, a solution of (R,S)-methyl 2-(2-chlorophenylsulfonyl)-2-azaspiro[3.3]heptane-5-carboxylate (112 mg, 340 µmol) in dioxane (0.3 mL) was added. The solution was stirred for 2 h at 100° C. and then at ambient temperature for 15 h. After cooling to 0° C., the reaction mixture was carefully diluted with ethyl acetate (1 mL) and an aqueous 1 M solution of sodium carbonate (1 mL) was carefully added. The aqueous layer was separated and was extracted with ethyl acetate (1 mL×2). The organic layers were washed with water (1 mL) and brine (1 mL), dried over sodium sulfate and concentrated under reduced pressure. The resulting residue was purified by chromatography (SiO$_2$; heptane:ethyl acetate 1:1) to give the title compound (118 mg, 80%) as a pale yellow oil. HRMS (EI): 432.1271 (exact mass calculated for $C_{22}H_{24}ClN_2O_3S$ ([M+H]$^+$)=432.1274).

c) (R)-2-(2-Chlorophenylsulfonyl)-N-(3-phenylpropyl)-2-azaspiro[3.3]heptane-5-carboxamide and (S)-2-(2-chlorophenylsulfonyl)-N-(3-phenylpropyl)-2-azaspiro[3.3]heptane-5-carboxamide (R,S)-2-(2-Chlorophenylsulfonyl)-N-(3-phenylpropyl)-2-azaspiro[3.3]heptane-5-carboxamide (140 mg, 323 µmol) was separated on chiral HPLC to afford (R)-2-(2-chlorophenylsulfonyl)-N-(3-phenylpropyl)-2-azaspiro[3.3]heptane-5-carboxamide (55 mg, 39%) as a colorless oil (MS (EI) m/e: 433.1 (M+H)+) and (S)-2-(2-chlorophenylsulfonyl)-N-(3-phenylpropyl)-2-azaspiro[3.3]heptane-5-carboxamide (53 mg, 38%) as a colorless oil (MS (EI) m/e: 433.1 (M+H)+).

Example 16 and 17

(R)-1-(2-(4-Chlorophenylsulfonyl)-2-azaspiro[3.3]heptan-5-yl)-3-(2,4-dichlorobenzyl)urea and (S)-1-(2-(4-Chlorophenylsulfonyl)-2-azaspiro[3.3]heptan-5-yl)-3-(2,4-dichlorobenzyl)urea

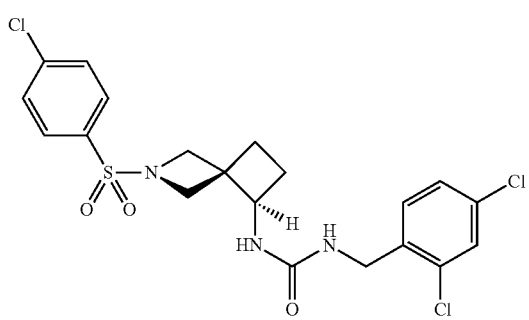

and

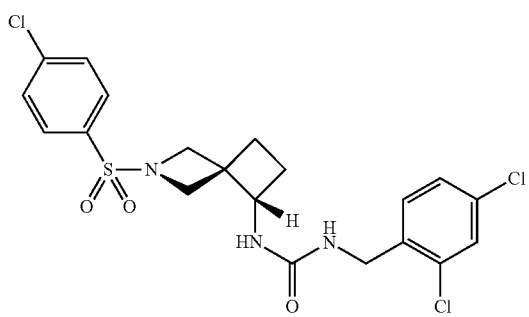

a) (R,S)-tert-Butyl 2-benzhydryl-2-azaspiro[3.3]heptan-5-ylcarbamate

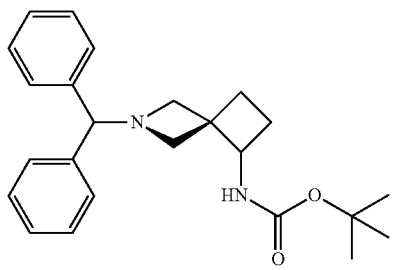

To a solution of (R,S)-2-benzhydryl-2-azaspiro[3.3]heptan-5-amine (1.31 g, 4.71 mmol) in methanol (10 mL) was added triethylamine (1.31 mL, 9.41 mmol) and Boc$_2$O (1.2 mL, 5.18 mmol). The reaction mixture was stirred at ambient temperature for 1 h and was then concentrated under reduced pressure. The residue was purified by chromatography (SiO$_2$; heptane:ethyl acetate 4:1 to 1:1) to give the title compound as a colorless foam. MS (EI) m/e: 379.3 ([M+H])$^+$.

b) (R,S)-5-(tert-Butoxycarbonylamino)-2-aza-spiro[3.3]heptane oxalate

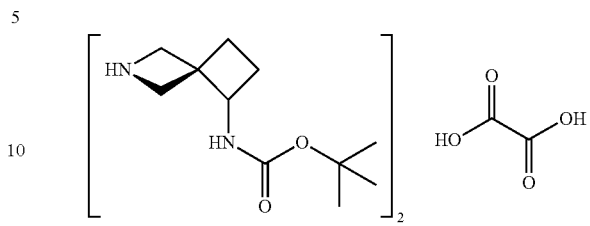

To a solution of (R,S)-tert-butyl 2-benzhydryl-2-azaspiro[3.3]heptan-5-ylcarbamate (1.23 g, 3.25 mmol) in methanol (40 mL), Pearlman's catalyst (20 wt. % loading, 913 mg, 1.3 mmol) was added at ambient temperature. A hydrogen atmosphere (balloon) was built up, and the mixture was stirred at ambient temperature for 3 h. The crude suspension was filtered over celite and the filter cake thoroughly washed with methanol, and the filtrate was concentrated under reduced pressure. To a solution of the intermediate free azetidine in diethylether (75 mL) a solution of anhydrous oxalic acid (146 mg, 1.62 mmol) in ethanol (0.3 mL), was added upon which a precipitate formed immediately. The solid was filtered and dried under reduced pressure to give the title compound (648 mg, 77%) as a colorless solid. MS (EI) m/e: 213.2 (M+H)$^+$.

c) (R,S)-tert-Butyl 2-(4-chlorophenylsulfonyl)-2-azaspiro[3.3]heptan-5-ylcarbamate

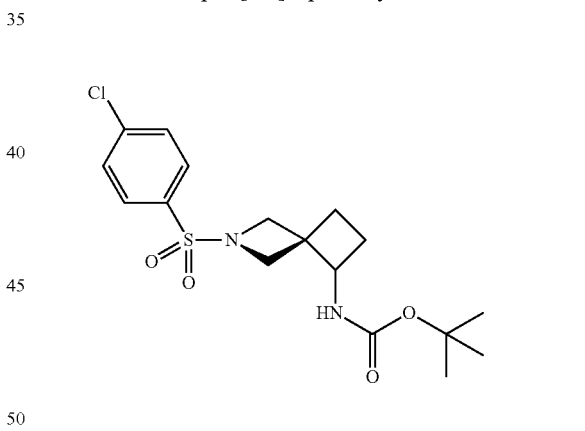

To a solution of (R,S)-5-(tert-butoxycarbonylamino)-2-aza-spiro[3.3]heptane oxalate (250 mg, 486 µmol) in dichloromethane (4 mL) was added at 0° C. triethylamine (271 µl, 1.94 mmol) followed by 4-chlorobenzene-1-sulfonyl chloride (226 mg, 1.07 mmol). The reaction was stirred at ambient temperature for 3 h and then diluted with dichloromethane (10 mL) and quenched with water (10 mL). The aqueous phase was extracted with dichloromethane and the combined organic phases were washed with brine, dried over sodium sulfate and concentrated under reduced pressure. The residue was purified by chromatography (SiO$_2$; heptane:ethyl acetate 2:1) to give the title product (295 mg, 78%) as a colorless foam. MS (EI) m/e: 387.1 (M+H)$^+$.

d) (R,S)-1-(2-(4-Chlorophenylsulfonyl)-2-azaspiro[3.3]heptan-5-yl)-3-(2,4-dichlorobenzyl)urea

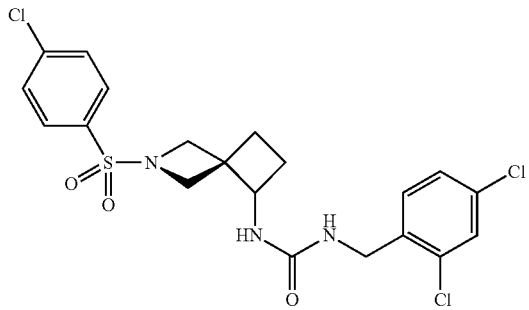

In analogy to the experimental procedure of example 5d) (R,S)-tert-butyl 2-(4-chlorophenylsulfonyl)-2-azaspiro[3.3]heptan-5-ylcarbamate (292 mg, 755 µmol) instead of tert-butyl 1-(4-fluorophenylsulfonyl)-1,6-diazaspiro[3.3]heptane-6-carboxylate was converted into the title compound (312 mg, 84%) which was obtained as a colorless foam. HRMS (EI): 487.0293 (exact mass calculated for $C_{20}H_{20}Cl_3N_3O_3S$ ([M]$^+$)=487.0291).

e) (R)-1-(2-(4-Chlorophenylsulfonyl)-2-azaspiro[3.3]heptan-5-yl)-3-(2,4-dichlorobenzyl)urea and (S)-1-(2-(4-Chlorophenylsulfonyl)-2-azaspiro[3.3]heptan-5-yl)-3-(2,4-dichlorobenzyl)urea (R,S)-1-(2-(4-Chlorophenylsulfonyl)-2-azaspiro[3.3]heptan-5-yl)-3-(2,4-dichlorobenzyl)urea (312 mg, 638 µmol) was separated on chiral HPLC to afford (R)-1-(2-(4-Chlorophenylsulfonyl)-2-azaspiro[3.3]heptan-5-yl)-3-(2,4-dichlorobenzyl)urea (124 mg, 39%) as a colorless solid (MS (EI) m/e: 490.0 (M+H)+) and (S)-1-(2-(4-Chlorophenylsulfonyl)-2-azaspiro[3.3]heptan-5-yl)-3-(2,4-dichlorobenzyl)urea (126 mg, 40%) as a colorless solid (MS (EI) m/e: 490.0 (M+H)+).

Example 18 rac-6-Benzoyl-3,6-diaza-bicyclo[3.2.0]heptane-3-carboxylic acid 2,4-dichloro-benzylamide

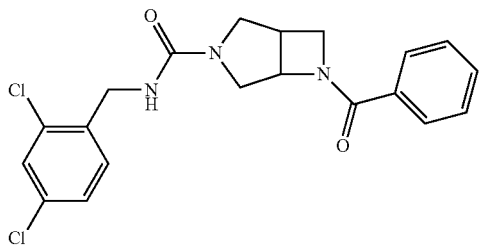 [SMILES: O=C(NCc1ccc(Cl)cc1Cl)N1CC2CN(C(=O)c3ccccc3)C2C1]

a) rac-3-(2,4-Dichloro-benzylcarbamoyl)-3,6-diaza-bicyclo[3.2.0]heptane-6-carboxylic acid tert-butyl ester

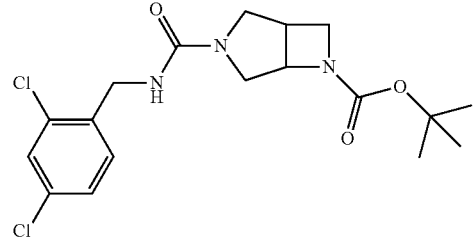 [SMILES: CC(C)(C)OC(=O)N1CC2CN(C(=O)NCc3ccc(Cl)cc3Cl)CC21]

In analogy to the experimental procedure of example 1a) rac-3,6-diaza-bicyclo[3.2.0]heptane-6-carboxylic acid tert-butyl ester instead of 6-(tert-butoxycarbonyl)-2,6-diaza-spiro[3.3]heptane oxalate was converted using 2,4-dichloro-1-(isocyanatomethyl)benzene into the title compound (691 mg, 88%) which was obtained as a colorless solid. MS (EI) m/e: 400.1 (M+H)+.

b) rac-3-(2,4-Dichloro-benzylcarbamoyl)-3,6-diaza-bicyclo[3.2.0]heptane

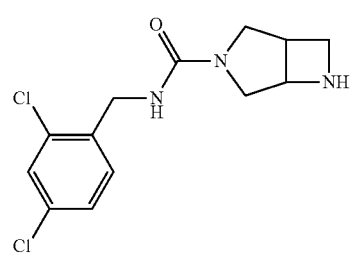 [SMILES: O=C(NCc1ccc(Cl)cc1Cl)N1CC2CNC2C1]

In analogy to the experimental procedure of example 1b) rac-3-(2,4-dichloro-benzylcarbamoyl)-3,6-diaza-bicyclo[3.2.0]heptane-6-carboxylic acid tert-butyl ester instead of 6-(2,4-dichloro-benzylcarbamoyl)-2,6-diaza-spiro[3.3]heptane-2-carboxylic acid tert-butyl ester was converted into the title compound (935 mg, 99%) which was obtained as a colorless solid. MS (EI) m/e: 300.3 (M+H)+.

c) rac-6-Benzoyl-3,6-diaza-bicyclo[3.2.0]heptane-3-carboxylic acid 2,4-dichloro-benzylamide In analogy to the experimental procedure of example 1c) rac-3-(2,4-Dichloro-benzylcarbamoyl)-3,6-diaza-bicyclo[3.2.0]heptane instead of 6-(2,4-dichloro-benzylcarbamoyl)-2,6-diaza-spiro[3.3]heptane using benzoyl chloride was converted into the title compound (92 mg, 84%) which was obtained as a white solid. MS (EI) m/e: 404.2 (M+H)+.

Example 19 rac-6-Benzenesulfonyl-3,6-diaza-bicyclo[3.2.0]heptane-3-carboxylic acid 2,4-dichloro-benzylamide

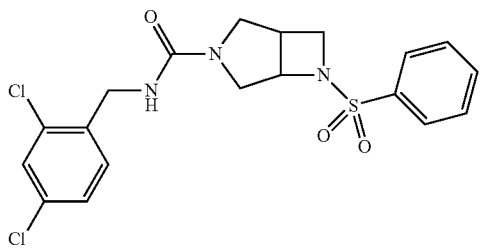 [SMILES: O=C(NCc1ccc(Cl)cc1Cl)N1CC2CN(S(=O)(=O)c3ccccc3)C2C1]

To a solution of rac-3,6-diaza-bicyclo[3.2.0]heptane-3-carboxylic acid 2,4-dichloro-benzylamide (150 mg, 270 µmol) in dichloromethane (6 mL) were added triethylamine (82 mg, 810 µmol), pyridine (1 mL) and benzenesulfonyl chloride (52 mg, 297 µmol). The reaction mixture was stirred at ambient temperature overnight before concentrating in vacuo. Purification by chromatography ($SiO_2$; dichloromethane:methanol 1:0 to 19:1) afforded the title compound (56 mg, 47%) as a colorless solid. MS (EI) m/e: 440.1 (M+H)+.

Example 20 rac-6-Pyrimidin-2-yl-3,6-diaza-bicyclo[3.2.0]heptane-3-carboxylic acid 2,4-dichloro-benzylamide

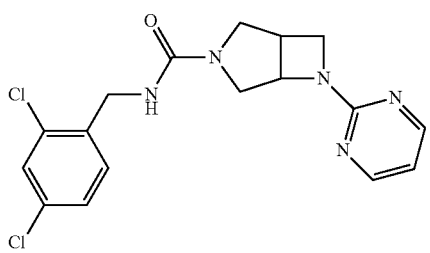 [SMILES: O=C(NCc1ccc(Cl)cc1Cl)N1CC2CN(c3ncccn3)C2C1]

To a solution of rac-3,6-diaza-bicyclo[3.2.0]heptane-3-carboxylic acid 2,4-dichloro-benzylamide (150 mg, 270 µmol) in toluene (6 mL) were added 2-bromopyrimidine (43 mg, 270 µmol) and triethylamine (27 mg, 270 µmol). After addition of tris(dibenzylideneacetone)dipalladium(0) (5 mg, 5 µmol), BINAP (10 mg, 16 µmol) and potassium tert-butylate (30 mg, 270 µmol) the reaction mixture was heated under an argon atmosphere to 110° C. for 20 h. It was filtered and concentrated in vacuo. Purification by chromatography ($SiO_2$; dichloromethane:methanol 1:0 to 9:1) afforded the title compound (26 mg, 25%) as a white solid. MS (EI) m/e: 378.3 (M+H)+.

Example 21 rac-4-[3-(2,4-Dichloro-benzylcarbamoyl)-3,6-diaza-bicyclo[3.2.0]hept-6-yl]-benzoic acid

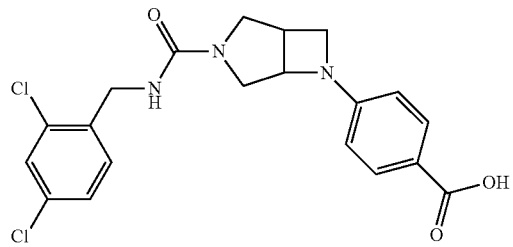 [SMILES: O=C(O)c1ccc(N2CC3CN(C(=O)NCc4ccc(Cl)cc4Cl)CC32)cc1]

a) rac-4-[3-(2,4-Dichloro-benzylcarbamoyl)-3,6-diaza-bicyclo[3.2.0]hept-6-yl]-benzoic acid ethyl ester

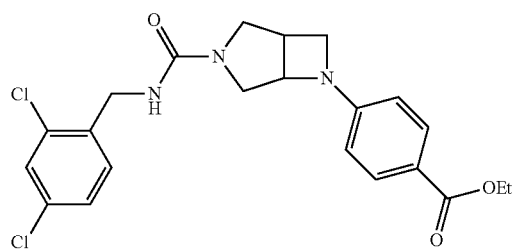 [SMILES: CCOC(=O)c1ccc(N2CC3CN(C(=O)NCc4ccc(Cl)cc4Cl)CC32)cc1]

In analogy to the experimental procedure of example 20) rac-3-(2,4-Dichloro-benzylcarbamoyl)-3,6-diaza-bicyclo [3.2.0]heptane using ethyl 4-bromobenzoate instead of 2-bromopyrimidine was converted into the title compound which was obtained as a white solid and directly used without further purification.

b) rac-4-[3-(2,4-Dichloro-benzylcarbamoyl)-3,6-diaza-bicyclo[3.2.0]hept-6-yl]-benzoic acid To a solution of rac-4-[3-(2,4-Dichloro-benzylcarbamoyl)-3,6-diaza-bicyclo[3.2.0]hept-6-yl]-benzoic acid ethyl ester (55 mg, 123 µmol) in methanol (2 mL) and tetrahydrofuran (2 mL) was added aqueous sodium hydroxide (1 M, 2 mL) and the reaction mixture was heated to 60° C. for 1 h. The solvents were partly removed by concentration in vacuo, tetrahydrofuran (2 mL) was added and filtration afforded the title compound (30 mg, 58%) as a white solid. MS (EI) m/e: 420.2 (M+H)+.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

BIOLOGICAL EXAMPLES

Example A

Human Soluble Epoxide Hydrolase Enzyme Assay

Test compounds (1.6 mM stock in DMSO) were diluted 3 fold in series in DMSO and 0.8 microliters per well were added into 384-well NBS microplates (Corning). Resorufin epoxide substrate (20 uM stock in DMSO) was diluted to 5 µM with Assay Buffer (25 mM bis-Tris-HCl, pH 7.0, 1 mM DTT and 0.2 mg/ml BSA) and 8 microliters per well were added to the microplates. Thirty two microliters per well of 3.6 nM soluble epoxide hydrolase in Assay Buffer was then added. The samples were incubated at room temperature and assay signals were monitored by reading excitation at 530 nm and emission fluorescence at 590 nm on a PlateVision (Zeiss) reader every 2 minutes for 8 times. The reaction rate, % inhibition and $IC_{50}$ values were calculated using AssayAnalyzer and Condoseo software (Genedata AG, Basel, Switzerland).

All the experiments were done in triplicates.

The compounds of the present invention were tested for their capacity to inhibit sEH activity. The Examples were tested in the above assay and found to have $IC_{50}$ of about 79 nM to about 2792 nM. Values for specific compounds are shown in Table 1.

The invention claimed is:

1. A compound of Formula (I):

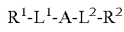

(I)

wherein

A is selected from the group consisting of Ia, and Ic:

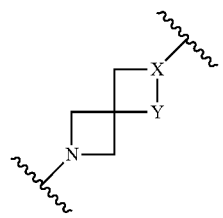

Ia wherein
X is N or CH;
Y is NH or $CH_2$; and

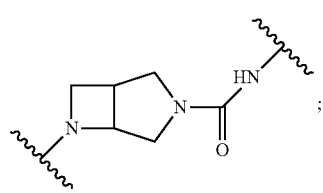

Ic wherein
$L^1$ is selected from the group consisting of a bond, $-(CH_2)_{1-3}-$, $-NH-(CH_2)_{0-3}-C(O)-$, $-(CH_2)_{0-3}-C(O)-$, $-(CH_2)_{0-3}-SO_2-$ and $-(CH_2)_{0-3}-NR^3-C(O)-$;
$L^2$ is selected from the group consisting of a bond, $-(CH_2)_{1-3}-$, $-(CH_2)_{0-3}-C(O)-NH-$, $-NH-(CH_2)_{0-3}-C(O)-NH-$, $-(CH_2)_{0-3}-C(O)-$, $-(CH_2)_{0-3}-SO_2-$ and $-(CH_2)_{0-3}-NR^3-C(O)-$;

$R^1$ is selected from the group consisting of phenyl, 5- or 6-membered heteroaryl, adamantyl and $-(CH_2)_{1-3}$-phenyl, wherein said phenyl, heteroaryl or adamantyl is unsubstituted or substituted by one to three $R^5$ groups;

$R^2$ is selected from the group consisting of phenyl, 5- or 6-membered heteroaryl and $-(CH_2)_{1-3}$-phenyl, wherein said phenyl or heteroaryl is unsubstituted or substituted by one to three $R^5$ groups;

$R^3$ is hydrogen or lower alkyl;

$R^4$ is hydrogen or lower alkyl; and $R^5$ is selected from the group consisting of halogen, lower alkyl, lower haloalkyl, lower haloalkoxy, and $-C(O)OR^4$, or a stereoisomer, tautomer or pharmaceutically acceptable salt thereof, with the proviso that said compound is not 2,6-bis[(4-methylphenyl)sulfonyl]-2,6-diazaspiro[3,3]heptane or 2-phenyl-6-(phenylmethyl)-2,6-diazaspiro[3,3]heptane, and the further provisos that when $L^2$ is $-C(O)-NH-$, $L^1$ is not $-CH_2-$; when $L^2$ is $-CH_2-$, $L^1$ is not a bond; when $L^2$ is $-SO_2-$, $L^1$ is not $-CH_2-$; and $L^1$ and $L^2$ are different.

2. The compound according to claim 1 selected from the group consisting of:

6-Benzoyl-2,6-diaza-spiro[3.3]heptane-2-carboxylic acid 2,4-dichloro-benzylamide;

4-[6-(2,4-Dichloro-benzylcarbamoyl)-2,6-diaza-spiro[3.3]hept-2-yl]-benzoic acid;

6-(2,4-Dichloro-benzenesulfonyl)-2,6-diaza-spiro[3.3]heptane-2-carboxylic acid benzylamide;

6-Pyrimidin-2-yl-2,6-diaza-spiro[3.3]heptane-2-carboxylic acid 2,4-dichloro-benzylamide;

rac-6-Benzoyl-3,6-diaza-bicyclo[3.2.0]heptane-3-carboxylic acid 2,4-dichloro-benzylamide;

rac-6-Benzenesulfonyl-3,6-diaza-bicyclo[3.2.0]heptane-3-carboxylic acid 2,4-dichloro-benzylamide;

rac-6-Pyrimidin-2-yl-3,6-diaza-bicyclo[3.2.0]heptane-3-carboxylic acid 2,4-dichloro-benzylamide; and rac-4-[3-(2,4-Dichloro-benzylcarbamoyl)-3,6-diaza-bicyclo[3.2.0]hept-6-yl]-benzoic acid, and pharmaceutically acceptable salts thereof.

3. The compound according to claim 1 selected from the group consisting of:

6-Benzoyl-2,6-diaza-spiro[3.3]heptane-2-carboxylic acid 2,4-dichloro-benzylamide;

6-(2,4-Dichloro-benzenesulfonyl)-2,6-diaza-spiro[3.3]heptane-2-carboxylic acid benzylamide; [3.3]heptane-5-carboxamide;

rac-6-Benzoyl-3,6-diaza-bicyclo[3.2.0]heptane-3-carboxylic acid 2,4-dichloro-benzylamide; and rac-6-Benzenesulfonyl-3,6-diaza-bicyclo[3.2.0]heptane-3-carboxylic acid 2,4-dichloro-benzylamide;

and pharmaceutically acceptable salts thereof.

4. The compound according to claim 1 wherein said compound is a compound according to formula IAa,

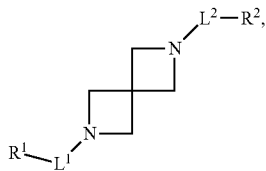

IAa

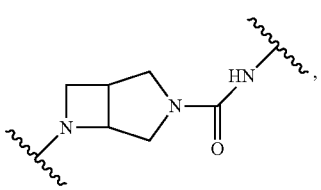

IAc wherein
$L^1$ is selected from the group consisting of a bond, —$(CH_2)_{0-3}$—C(O)—, and —$(CH_2)_{0-3}$—$SO_2$—;
$L^2$ is —C(O)—$(CH_2)_{0-3}$—NH—;
$R^1$ is phenyl or 5- or 6-membered heteroaryl, wherein said phenyl or heteroaryl is unsubstituted or substituted by one $R^5$ group;
$R^2$ is phenyl or —$(CH_2)_{1-3}$-phenyl, wherein said phenyl is unsubstituted or substituted by two $R^5$ groups;
$R^4$ is hydrogen; and
$R^5$ is —C(O)$OR^4$; or
a stereoisomer, tautomer or pharmaceutically acceptable salt thereof.

5. The compound of according to claim 4 selected from the group consisting of:
   6-Benzoyl-2,6-diaza-spiro[3.3]heptane-2-carboxylic acid 2,4-dichloro-benzylamide;
   4-[6-(2,4-Dichloro-benzylcarbamoyl)-2,6-diaza-spiro[3.3]hept-2-yl]-benzoic acid;
   6-(2,4-Dichloro-benzenesulfonyl)-2,6-diaza-spiro[3.3]heptane-2-carboxylic acid benzylamide;
   6-Pyrimidin-2-yl-2,6-diaza-spiro[3.3]heptane-2-carboxylic acid 2,4-dichloro-benzylamide; and
   pharmaceutically acceptable salts thereof.

6. The compound according to claim 1 wherein said compound is a compound according to Formula IAc, wherein:
$L^1$ is selected from the group consisting of a bond, —$(CH_2)_{0-3}$—C(O)— and —$(CH_2)_{0-3}$—$SO_2$—;
$L^2$ is —$(CH_2)_{1-3}$—;
$R^1$ is phenyl or 5- or 6-membered heteroaryl, wherein said phenyl or heteroaryl is unsubstituted or substituted by one $R^5$ group;
$R^2$ is phenyl, wherein said phenyl is unsubstituted or substituted by two $R^5$ groups;
$R^4$ is hydrogen or lower alkyl; and
$R^5$ is halogen or —C(O)$OR^4$, or
a stereoisomer, tautomer or pharmaceutically acceptable salt thereof.

7. The compound according to claim 6 selected from the group consisting of:
   rac-6-Benzoyl-3,6-diaza-bicyclo[3.2.0]heptane-3-carboxylic acid 2,4-dichloro-benzylamide;
   rac-6-Benzenesulfonyl-3,6-diaza-bicyclo[3.2.0]heptane-3-carboxylic acid 2,4-dichloro-benzylamide;
   rac-6-Pyrimidin-2-yl-3,6-diaza-bicyclo[3.2.0]heptane-3-carboxylic acid 2,4-dichloro-benzylamide;
   rac-4-[3-(2,4-Dichloro-benzylcarbamoyl)-3,6-diaza-bicyclo[3.2.0]hept-6-yl]-benzoic acid; and
   pharmaceutically acceptable salts thereof.

8. A pharmaceutical composition comprising the compound according to claim 1 and a pharmaceutically acceptable carrier.

\* \* \* \* \*

UNITED STATES PATENT AND TRADEMARK OFFICE
CERTIFICATE OF CORRECTION

| | | |
|---|---|---|
| PATENT NO. | : 9,139,593 B2 | Page 1 of 1 |
| APPLICATION NO. | : 14/328033 | |
| DATED | : September 22, 2015 | |
| INVENTOR(S) | : Simona M. Ceccarelli et al. | |

It is certified that error appears in the above-identified patent and that said Letters Patent is hereby corrected as shown below:

Please correct Title page, (71) Applicant to read as follows:

-- HOFFMANN-LA ROCHE INC., Nutley, NJ (US) --

Signed and Sealed this
Nineteenth Day of January, 2016

Michelle K. Lee
*Director of the United States Patent and Trademark Office*